(12) United States Patent
Lampropoulos et al.

(10) Patent No.: US 10,398,420 B2
(45) Date of Patent: Sep. 3, 2019

(54) MEDICAL PLUG DELIVERY DEVICES WITH A ROTATABLE MAGAZINE AND RELATED COMPONENTS AND METHODS

(71) Applicant: Merit Medical Systems, Inc., South Jordan, UT (US)

(72) Inventors: Fred Lampropoulos, Salt Lake City, UT (US); Jim Mottola, West Jordan, UT (US); Richard P. Jenkins, Bluffdale, UT (US); Gregory R. McArthur, Sandy, UT (US); Kenneth Sykes, Bluffdale, UT (US); Christopher Cindrich, Draper, UT (US); Mark Garcia, Wilmington, DE (US)

(73) Assignee: Merit Medical Systems, Inc., South Jordan, UT (US)

( * ) Notice: Subject to any disclaimer, the term of this patent is extended or adjusted under 35 U.S.C. 154(b) by 132 days.

(21) Appl. No.: 15/479,149

(22) Filed: Apr. 4, 2017

(65) Prior Publication Data
US 2017/0281141 A1    Oct. 5, 2017

Related U.S. Application Data

(60) Provisional application No. 62/354,493, filed on Jun. 24, 2016, provisional application No. 62/317,914, (Continued)

(51) Int. Cl.
| | |
|---|---|
| *A61B 17/00* | (2006.01) |
| *A61M 5/00* | (2006.01) |
| *A61M 5/32* | (2006.01) |
| *A61M 37/00* | (2006.01) |
| *A61M 5/24* | (2006.01) |

(52) U.S. Cl.
CPC ........... *A61B 17/0057* (2013.01); *A61M 5/00* (2013.01); *A61M 5/3294* (2013.01);
(Continued)

(58) Field of Classification Search
CPC ...... A61M 5/3294; A61M 2017/00893; A61M 2005/005; A61M 2005/2485;
(Continued)

(56) References Cited

U.S. PATENT DOCUMENTS

| | | | |
|---|---|---|---|
| 4,673,387 A | * 6/1987 | Phillips | ............ A61M 37/0069 604/62 |
| 4,842,592 A | 6/1989 | Caggiani et al. | |

(Continued)

FOREIGN PATENT DOCUMENTS

| | | |
|---|---|---|
| EP | 2514456 | 10/2012 |
| WO | 2006119256 | 11/2006 |

(Continued)

OTHER PUBLICATIONS

International Search Report and Written Opinion dated Jul. 17, 2017 for PCT/US2017/025986.
(Continued)

*Primary Examiner* — Eric J Rosen
*Assistant Examiner* — Andrew P. Restaino
(74) *Attorney, Agent, or Firm* — Stoel Rives LLP

(57) ABSTRACT

Medical devices for delivering compositions or medical articles to a patient are disclosed. The medical plug delivery devices can include a fluid delivery device (e.g., a syringe), a frame, and a rotatable magazine. The rotatable magazine can include a plurality of chambers that each hold a composition or a medical article (e.g., a medical plug). By rotating the rotatable magazine relative to the frame, material within the chambers of the rotatable magazine can be sequentially deployed to a patient.

14 Claims, 20 Drawing Sheets

Related U.S. Application Data filed on Apr. 4, 2016, provisional application No. 62/317,830, filed on Apr. 4, 2016.

(52) U.S. Cl.
CPC .............................. *A61M 37/0069* (2013.01); *A61B 2017/0053* (2013.01); *A61B 2017/00115* (2013.01); *A61B 2017/00539* (2013.01); *A61B 2017/00623* (2013.01); *A61B 2017/00654* (2013.01); *A61B 2017/00659* (2013.01); *A61B 2017/00893* (2013.01); *A61M 2005/005* (2013.01); *A61M 2005/2485* (2013.01)

(58) Field of Classification Search
CPC . A61M 37/0069; A61M 5/00; A61B 17/0057; A61B 2017/00115; A61B 2017/0053; A61B 2017/00539; A61B 2017/00623; A61B 2017/00654; A61B 2017/00659; A61B 2017/00893
USPC .................................. 606/213, 123
See application file for complete search history.

(56) References Cited

U.S. PATENT DOCUMENTS

| | | | |
|---|---|---|---|
| 5,318,522 A | 6/1994 | D'Antonio | |
| 5,727,320 A * | 3/1998 | Shepherd | B26B 5/001 30/125 |
| 8,915,941 B2 | 12/2014 | Obermiller et al. | |
| 9,545,282 B2 * | 1/2017 | Mathur | A61B 17/8825 |
| 2005/0124999 A1 | 6/2005 | Teitelbaum et al. | |
| 2006/0065271 A1 | 3/2006 | Ishizeki et al. | |
| 2006/0264967 A1 * | 11/2006 | Ferreyro | A61B 17/00234 606/93 |
| 2008/0312604 A1 * | 12/2008 | Boesen | A61M 5/008 604/207 |
| 2013/0079812 A1 | 3/2013 | Duncan et al. | |
| 2013/0296828 A1 | 11/2013 | Schon et al. | |
| 2014/0303744 A1 | 10/2014 | Evans et al. | |
| 2015/0025469 A1 | 1/2015 | Larsen et al. | |
| 2015/0142003 A1 | 5/2015 | Giersch et al. | |
| 2016/0262737 A1 | 9/2016 | Paul, Jr. et al. | |

FOREIGN PATENT DOCUMENTS

| | | | | |
|---|---|---|---|---|
| WO | WO-2015025178 A1 * | 2/2015 | ............ | A61B 17/29 |
| WO | 2017173378 | 10/2017 | | |

OTHER PUBLICATIONS

International Search Report and Written Opinion dated Aug. 17, 2017 for PCT/US2017/025565.

International Search Report and Written Opinion dated Apr. 23, 2019 for PCT/US2018/065495.

\* cited by examiner

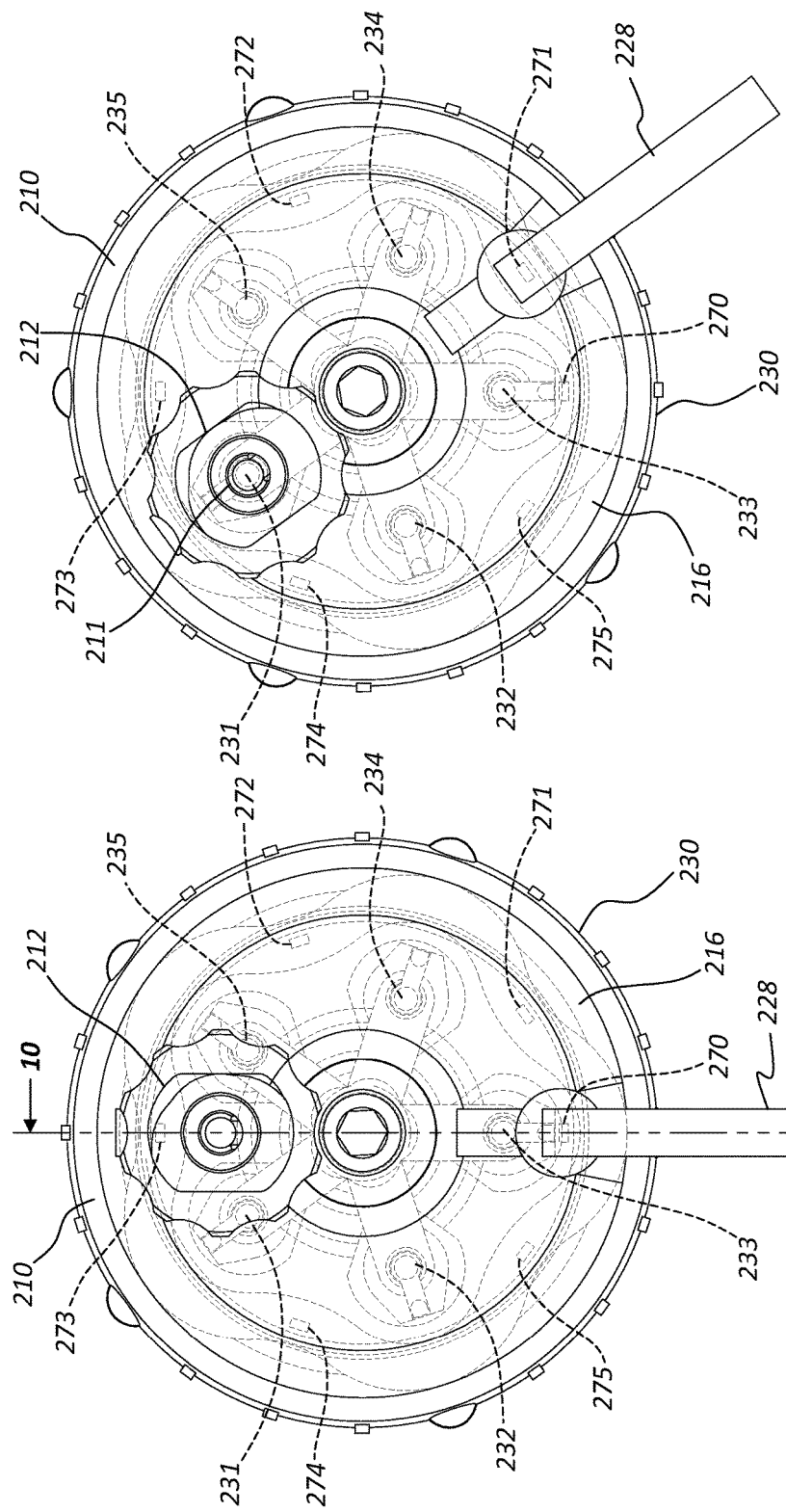

MEDICAL PLUG DELIVERY DEVICES WITH A ROTATABLE MAGAZINE AND RELATED COMPONENTS AND METHODS

CROSS-REFERENCE TO RELATED APPLICATIONS

This application claims priority to U.S. Provisional Application No. 62/317,914 filed Apr. 4, 2016, titled DEVICES WITH A ROTATABLE MAGAZINE FOR DELIVERING MEDICAL PLUGS, and to U.S. Provisional Application No. 62/354,493 filed Jun. 24, 2016, titled MEDICAL DELIVERY DEVICES WITH A ROTATABLE MAGAZINE AND RELATED COMPONENTS AND METHODS, and to U.S. Provisional Application No. 62/317,830 filed Apr. 4, 2016, titled DEVICES FOR DELIVERING MULTIPLE MEDICAL PLUGS, the entire contents of each application are hereby incorporated by reference in their entireties.

TECHNICAL FIELD

The present disclosure relates generally to the field of medical devices. More particularly, some embodiments relate to medical devices for delivering compositions or medical articles (e.g., medical plugs) to a patient. Related methods are also disclosed.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 13 is a proximal end view of the medical plug delivery device of FIGS. 8-12 with the selector in a first position.

FIG. 14 is a proximal end view of the medical plug delivery device of FIGS. 8-13 with the selector in a second position.

DETAILED DESCRIPTION

Figure 1:
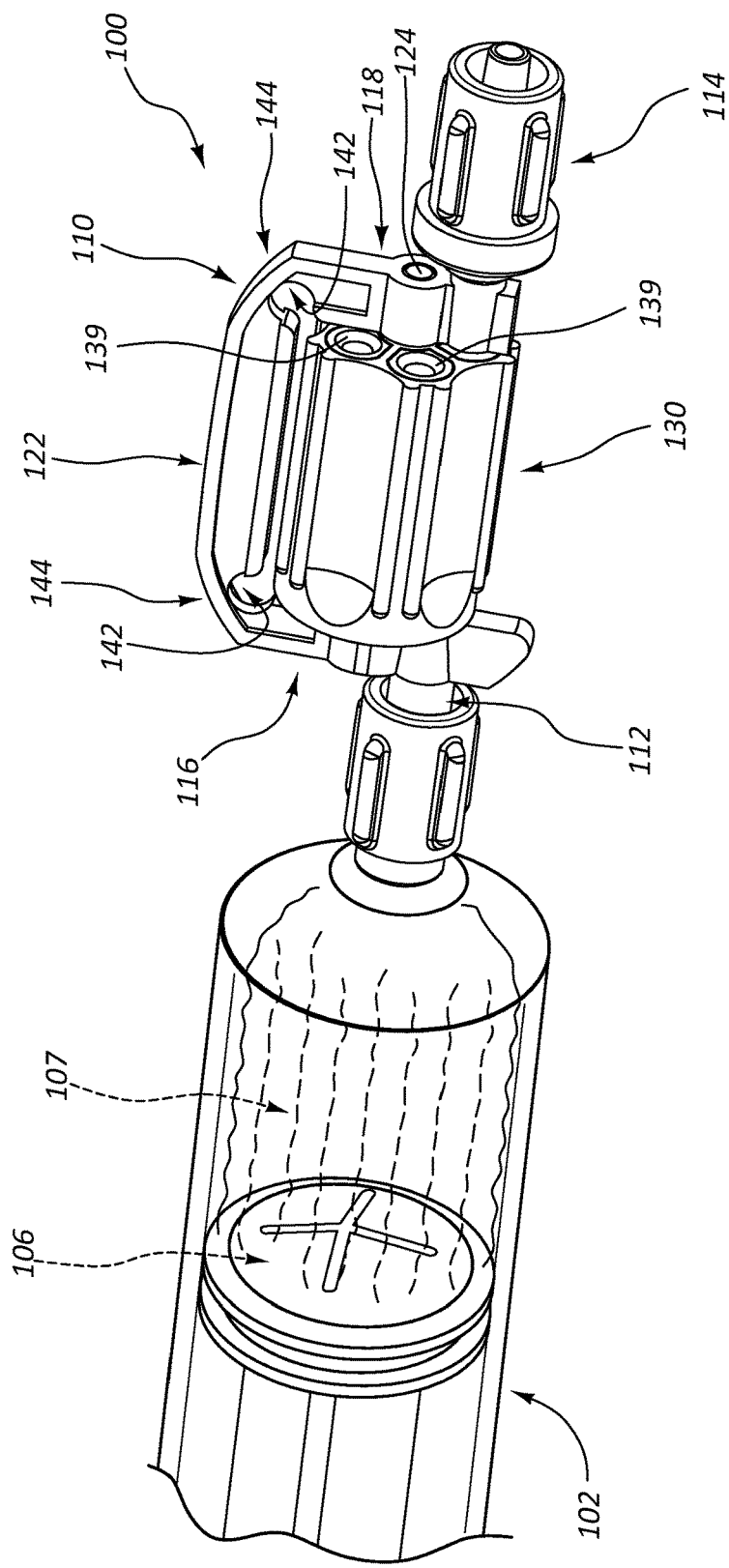
FIG. 1 is a perspective view of a medical plug delivery device.

Medical plug delivery devices may be used to deliver compositions and/or medical articles to a patient. For example, some medical plug delivery devices may be used to deliver medical plugs (such as pledgets) into a patient's body. Medical plugs may be inserted into voids to, inter alia, partially or completely fill one or more wound sites, to occlude the passage of fluid through a lumen, to induce blood coagulation, to prevent or reduce leakage of biological fluid, and/or to provide a scaffold to promote and/or permit tissue growth.

For instance, during a biopsy procedure, a practitioner may insert an introducer sheath into a patient by placing a trocar within an introducer sheath such that a pointed distal end of the trocar protrudes from the distal end of the introducer sheath. With the pointed end of the trocar protruding from the introducer sheath, the trocar and the introducer sheath may together be inserted into the patient. Once the introducer sheath is positioned within the patient, the trocar may be withdrawn from the introducer sheath. At this stage of the procedure, the introducer sheath provides a conduit that allows access to a patient's internal bodily tissue.

A cutting device (e.g., a needle or some other device configured to obtain bodily samples) may then be inserted through the introducer sheath. Once the cutting device reaches the internal tissue, the cutting device may be used to excise (e.g., cut out) internal tissue from the patient. Such excision may leave behind a void in the space that was occupied by internal tissue.

In some circumstances, it may be advantageous to deliver one or more medical plugs into the void created by tissue that was excised during the biopsy procedure. For example, in some embodiments, one or more medical plugs may be inserted into the void to at least partially fill the space created by the void, to promote blood coagulation at the wound site, and/or to provide a scaffold to promote or permit tissue regrowth.

Medical plugs may be inserted into a void in other medical procedures as well. For example, medical plugs may be delivered to block fluid flow through a lumen. In other words, medical plugs may be delivered as embolic agents to prevent the flow of fluid to a particular location. Medical plugs may be delivered to various other locations in a patient's body, or may be delivered under alternative circumstances or for different purposes.

Some medical plug delivery devices and related components, as described in greater detail below, may be configured to facilitate delivery of multiple medical articles (e.g., medical plugs) into a patient's body. The use of a single device to deliver multiple medical plugs may provide significant advantages, such as facilitating delivery of multiple plugs to fill a relatively large site, or facilitating the delivery of single medical plugs to multiple locations (e.g., wound sites) within the patient. In some circumstances, the medical plug delivery devices are designed to facilitate both wetting (e.g., hydration) and delivery of the medical plugs through a lumen to one or more interior regions within a patient.

Alternatively, some medical plug delivery devices disclosed herein may be used to deliver one or more medicaments (e.g., drugs) to a patient. In some embodiments, one or more medicaments may be disposed (e.g., preloaded) as a solid (e.g., a powder) within one or more chambers of a magazine of the medical plug delivery device. The medicaments may then be hydrated and delivered to a patient. In some circumstances, such devices may be used to deliver multiple doses of a medicament or to select the appropriate dose from among various doses of the medicament. In some embodiments, each chamber may include a different medicament.

One of ordinary skill in the art, with the benefit of this disclosure, will understand that this disclosure relates broadly to the delivery of compositions and/or medical articles (e.g., medical plugs) for various purposes, and is not limited to the specific contexts discussed herein. Further, although some medical plug delivery devices are described below with specific reference to the delivery of medical plugs, such devices may alternatively, in some cases, be used to deploy some other medical article(s) or medicament(s).

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any connection or coupling between two or more entities. Two components may be coupled to each other even though they are not in direct contact with each other. For example, two components may be coupled to each other through an intermediate component. The phrase "fluid communication" is broad enough to refer to arrangements in which a fluid can flow from one element to another element when the elements are in fluid communication with each other.

The terms "proximal" and "distal" are opposite directional terms. The distal end of a device or component is the end of the component that is furthest from the practitioner during ordinary use. The proximal end refers to the opposite end, or the end nearest the practitioner during ordinary use. The term "void" relates to regions or openings within a patient's body to which a medical plug may be delivered.

Figure 2:
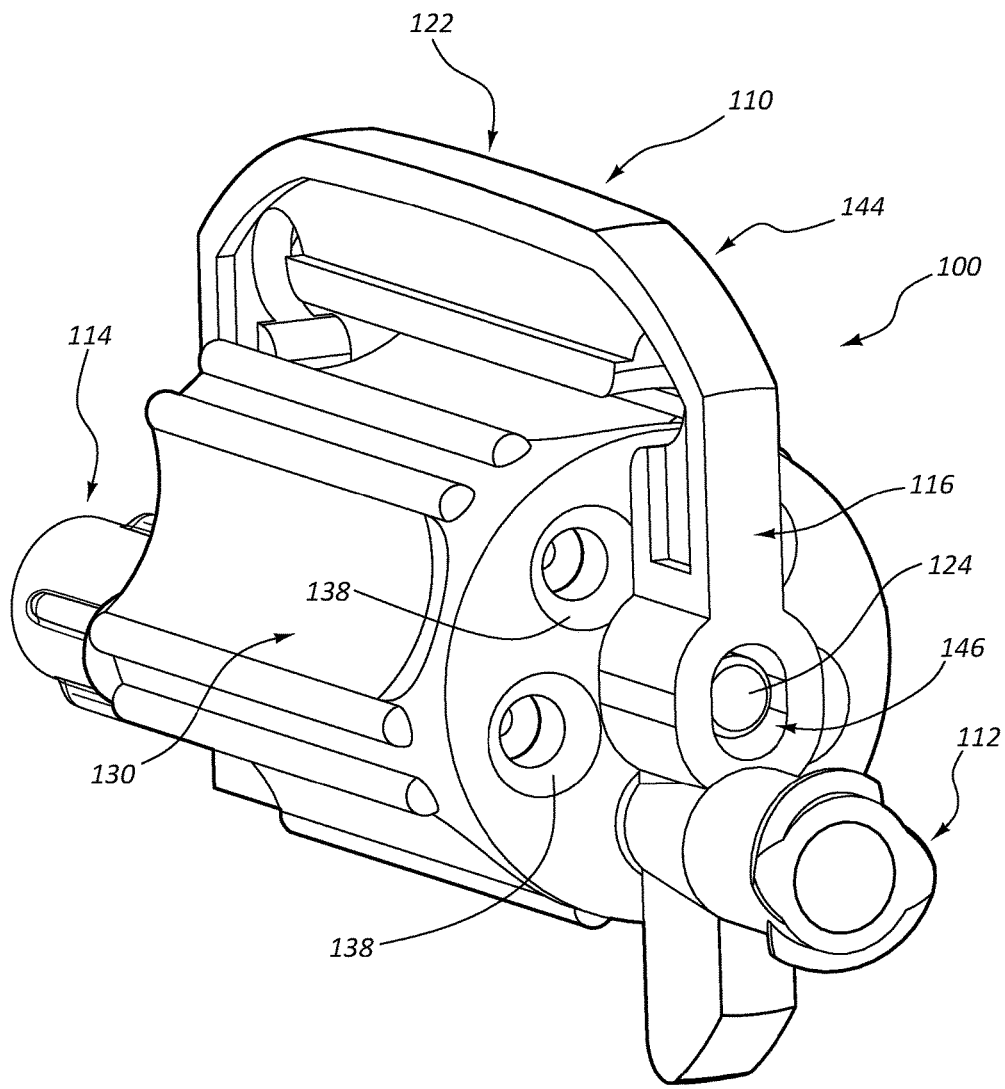
FIG. 2 is another perspective view of the medical plug delivery device of FIG. 1, with the syringe removed for clarity.
Figure 3:
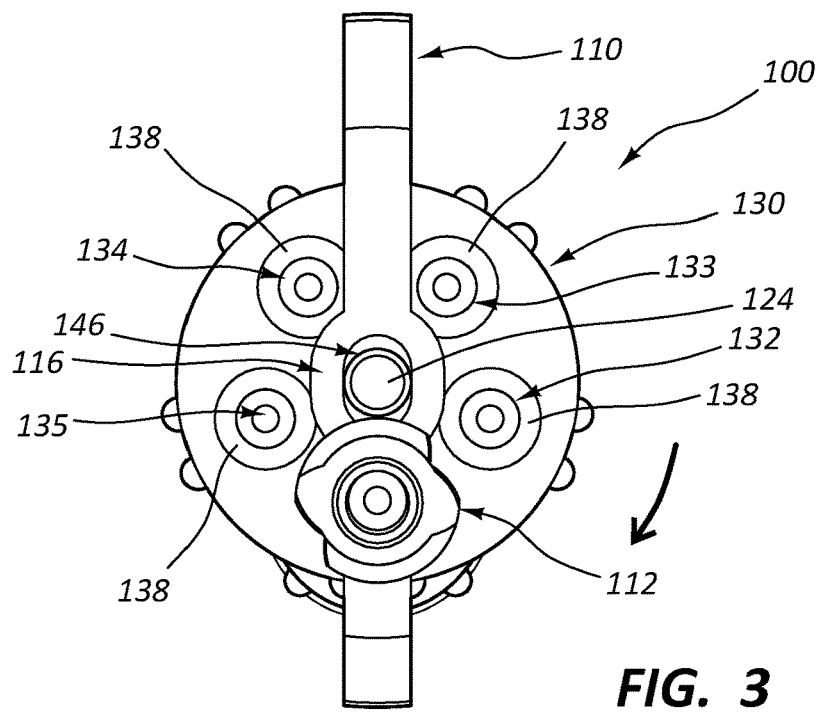
FIG. 3 is a back end view showing a proximal end of the medical plug delivery device of FIGS. 1-2, with the syringe removed for clarity.
Figure 4:
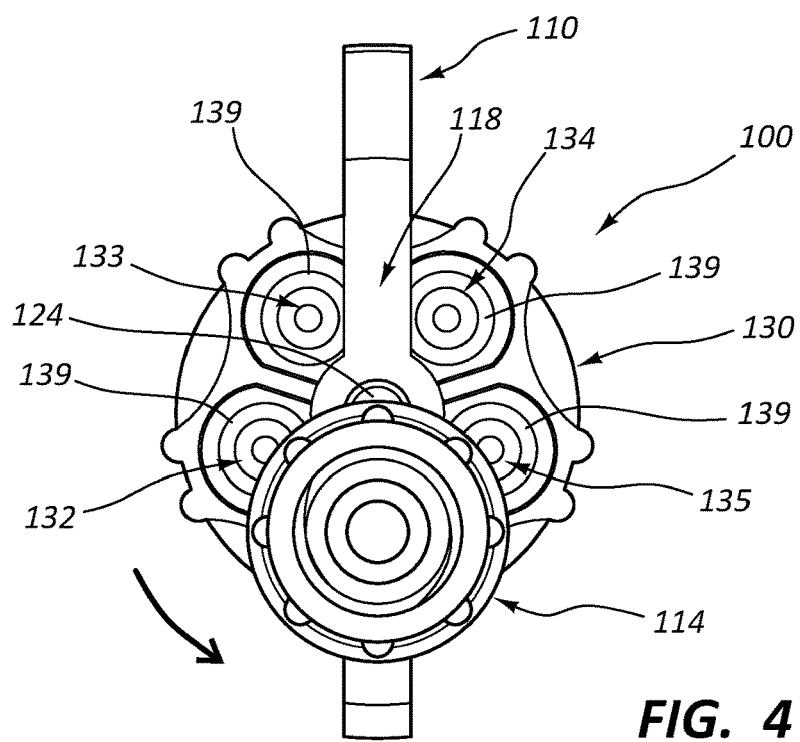
FIG. 4 is a front end view showing a distal end of the medical plug delivery device of FIGS. 1-3, with the syringe removed for clarity.
Figure 5:
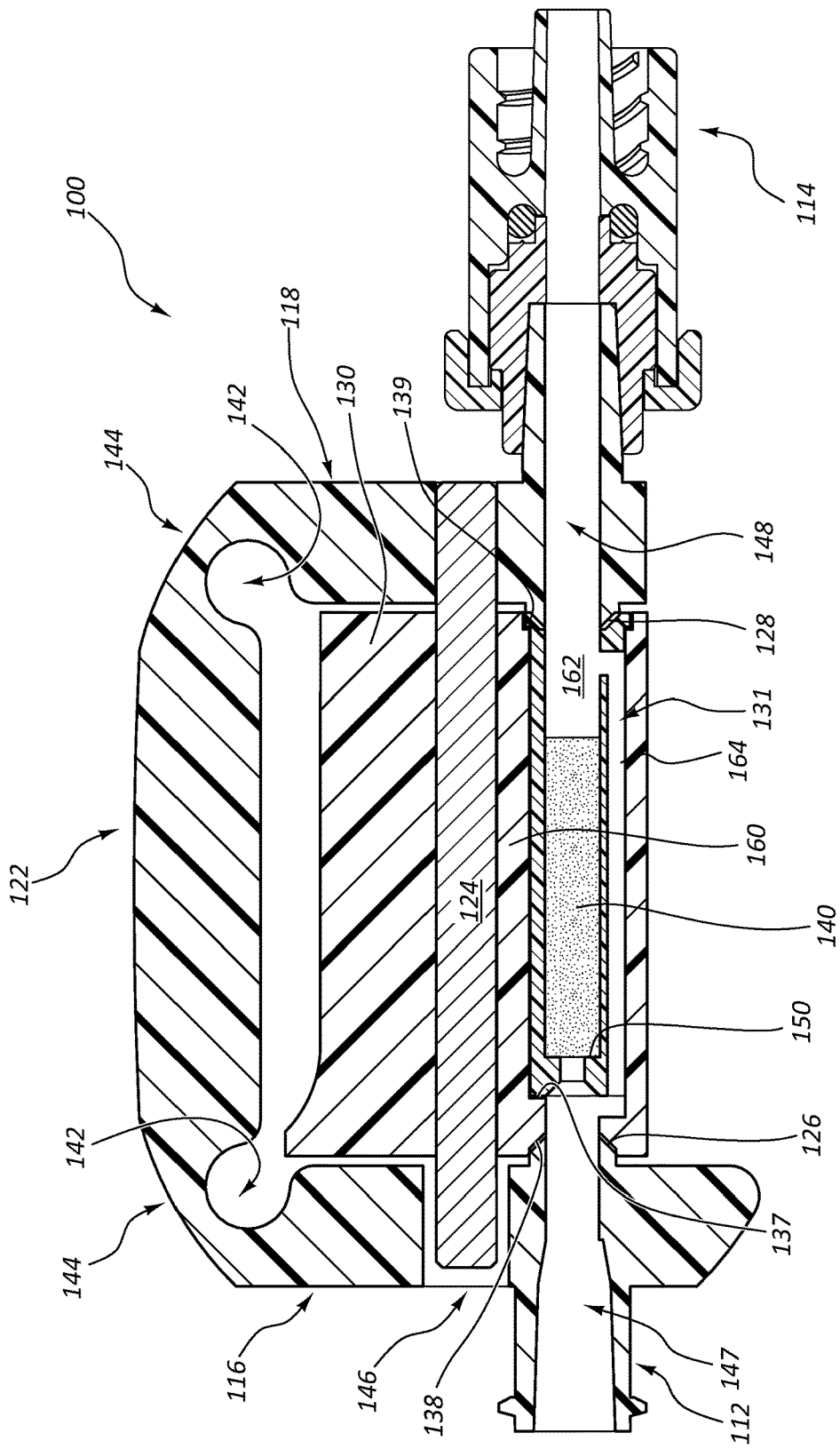
FIG. 5 is a cross-sectional view of a portion of the medical plug delivery device of FIGS. 1-4.
Figure 6:
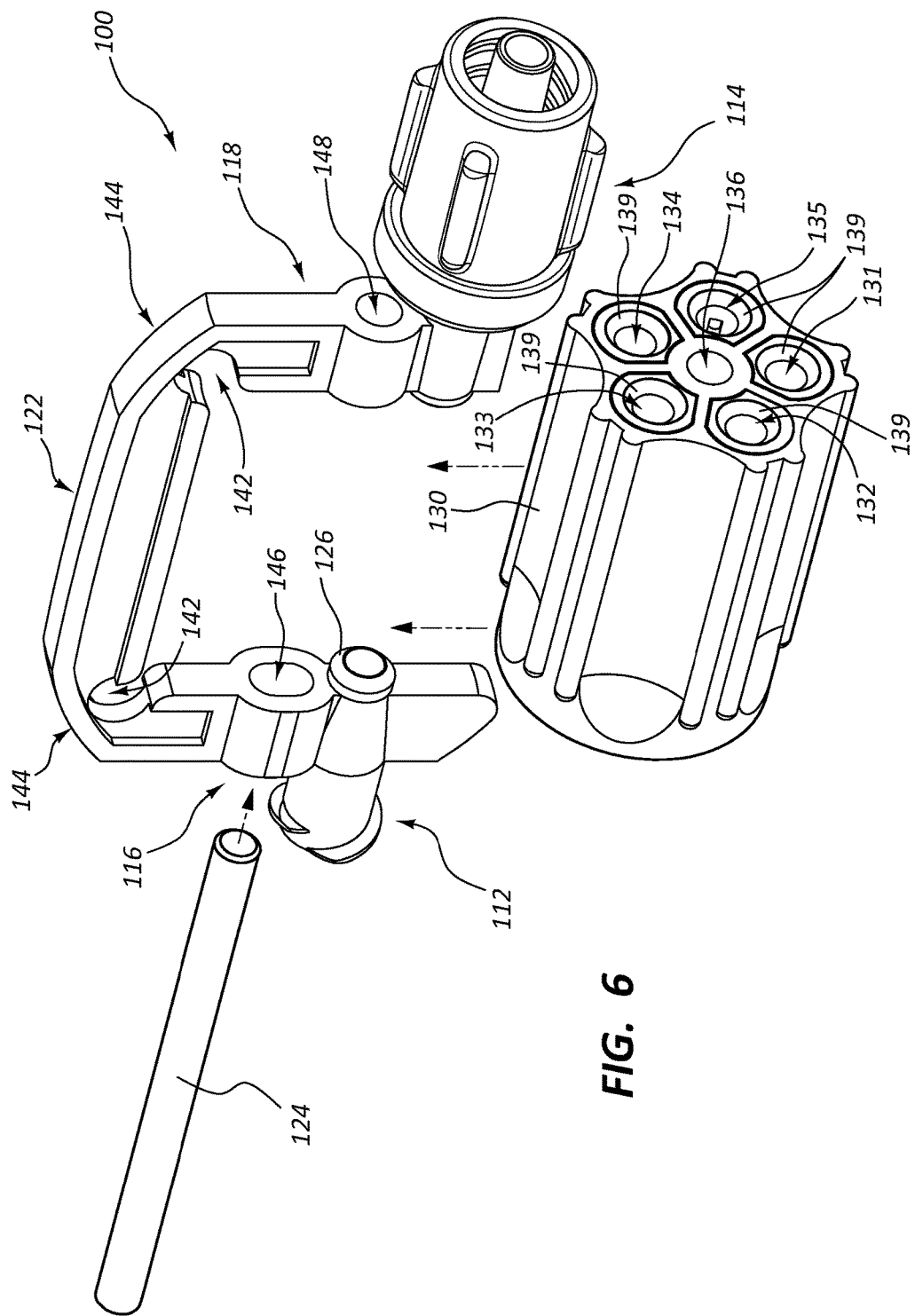
FIG. 6 is an exploded view of a portion of the medical plug delivery device of FIGS. 1-5.
Figure 7:
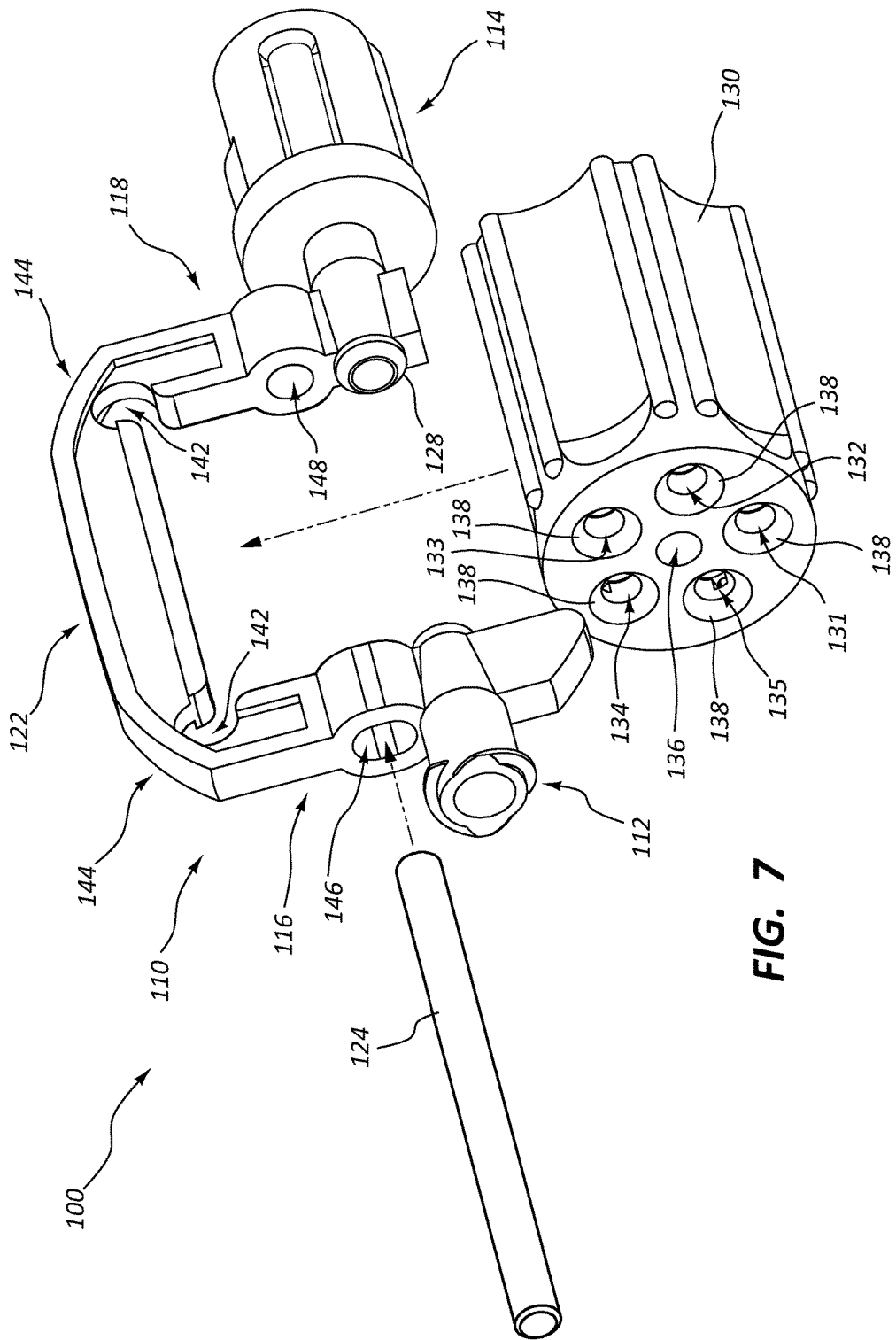
FIG. 7 is another exploded view of a portion of the medical plug delivery device of FIGS. 1-6.

FIGS. 1-7 provide alternative views of a medical plug delivery device 100 (or portions thereof) for delivering compositions and/or medical articles to a patient. More particularly, FIG. 1 provides a perspective view of the medical plug delivery device 100. FIG. 2 provides an alternative perspective view of the medical plug delivery device 100, with a syringe 102 removed for clarity. FIG. 3 provides a proximal end-on view of the medical plug delivery device 100, with the syringe 102 removed for clarity. FIG. 4 provides a distal end-on view of a portion of the medical plug delivery device 100, with the syringe 102 removed for clarity. FIG. 5 is a cross-sectional view of a portion of the medical plug delivery device 100. FIGS. 6 and 7 provide alternative exploded views of a portion of the medical plug delivery device 100.

As depicted in FIGS. 1-7, the medical plug delivery device 100 may include a fluid delivery device such as the syringe 102, a frame 110, an elongate shaft 124, and a rotatable magazine 130.

The syringe 102 may include a plunger 106 that is configured to be at least partially disposed within the body of the syringe 102 such that advancement and retraction of the plunger 106 cause displacement of fluid within a reservoir 107 of the syringe 102. The syringe 102 may be configured to couple to a proximal end of the frame 110. For example, in the depicted embodiment, the syringe 102 includes a male Luer lock connection at its distal end. In some embodiments, the syringe 102 is a standard, commercially available syringe. The syringe 102 may be capable of holding enough fluid to facilitate deployment of multiple medical compositions or articles (e.g., medicaments or medical plugs 140) into a patient. For example, in some embodiments, the syringe 102 is capable of holding at least 3 mL, at least 5 mL, at least 10 mL and/or at least 15 mL of fluid. In some embodiments, the syringe 102 is a vacuum lock syringe that allows practitioners to lock the plunger 106 at multiple positions along the body of the syringe 102. In other embodiments, the syringe 102 does not include a vacuum lock.

The frame 110 may include a proximal portion 116, a distal portion 118, and a connecting region 122 that is disposed between the proximal portion 116 and the distal portion 118. The proximal portion 116 may include a proximal adaptor 112 and a proximal channel 147. The distal portion 118 may include a distal adaptor 114 and the distal channel 148.

The proximal adaptor 112 may be configured to couple to the distal end of the syringe 102. For example, in the depicted embodiment, the proximal adaptor 112 of the frame 110 is a female Luer connection that is designed to couple to (e.g., form a fluid-tight connection with) the male Luer connection at the distal end of the syringe 102.

The proximal channel 147 and the distal channel 148 may be configured to provide portions of a fluid flow path. The fluid flow path may allow fluid to flow sequentially from the reservoir 107 of the syringe 102 to the proximal channel 147, from the proximal channel 147 to a first chamber 131 of the rotatable magazine 130, from the chamber 131 of the rotatable magazine 130 to the distal channel 148, and from the distal channel 148 to the patient. The fluid flow path may also allow fluid flow in the reverse direction, i.e., from the distal channel 148, through the chamber 131 of the rotatable magazine 130, through the proximal channel 147 to the reservoir 107 of the syringe 102.

In the depicted embodiment, the proximal channel 147 and the distal channel 148 are co-linear with one another such that the proximal channel 147 and the distal channel 148 are fixedly aligned. The connecting region 122 that is disposed between the proximal channel 147 and the distal channel 148 is not co-linear with the proximal channel 147 and the distal channel 148. For example, in the depicted embodiment, the frame 110 is bent into a C-shaped structure such that the connecting region 122 is offset from the proximal channel 147 and the distal channel 148.

The frame 110 may be coupled to the elongate shaft 124, which may be cylindrical in shape. The elongate shaft 124 may be made from any suitable material, such as steel. In the depicted embodiment, a first end of the elongate shaft 124 is attached (e.g., via an adhesive) to the frame 110, while a second end of the elongate shaft 124 (i.e., an end of the elongate shaft 124 that is disposed opposite the first end) is not attached to the frame 110. Instead, in the depicted embodiment, the frame 110 includes a cavity 146 for receiving (but not attaching to) the second end of the elongate shaft 124. The cavity 146 may be generally elongate in shape such that the cavity 146 is longer in the elongated direction than the diameter of the elongate shaft 124. The cavity 146 may be elongated to permit deflection of the frame 110 as the rotatable magazine 130 is rotated relative to the frame 110. In other words, as described below, the cavity 146 may permit deflection of the frame 110 as the medical plug delivery device 100 transitions from a configuration in which a first chamber 131 is aligned with both the proximal channel 147 and the distal channel 148 to a configuration in which a second chamber 132 is aligned with both the proximal channel 147 and the distal channel 148.

In some embodiments, the frame 110 includes one or more notches 142. The one or more notches 142 may decrease the amount of material at one or more regions (e.g., at one or more corners) of the frame 110, thereby creating one or more flex points 144 that allow for increased flexibility of the frame 110. The frame 110 may be made from or comprise any suitable resilient material, such as a plastic.

The frame 110 may also include a distal adaptor 114 that is configured to couple to an elongate tube, such as an introducer sheath or catheter that is in fluid communication with an interior of a patient. In some embodiments, the distal adaptor 114 is a simple male Luer connection. Such a simple connection may be formed integrally with the frame 110. In other embodiments, the distal adaptor 114 includes a male Luer lock connection that is configured to rotate independent of the remainder of the frame 110.

In some embodiments, the frame 110 of the medical plug delivery device 100 may include a plurality of caps (not shown). The caps may be configured to seal a composition or medical plug within a chamber 131, 132, 133, 134, 135 of the rotatable magazine 130. For example, in some embodiments, the frame 110 comprises a first hub with a first plurality of spokes that extend therefrom. In some embodiments, the frame 110 further comprises a second hub with a second plurality of spokes that extend therefrom. Each spoke of the first and/or second plurality of spokes may be coupled to a cap. In some embodiments, the caps may interact with sloped surfaces 138, 139 of the rotatable magazine 130 to form a seal that prevents a composition or article from escaping from a chamber 131, 132, 133, 134, 135. Such caps may interact with the sloped surfaces 138, 139 in a manner similar to that described below in connection with protrusions 126, 128. In some embodiments, the hubs are centered about the elongate shaft 124 of the medical plug delivery device 100.

The rotatable magazine 130 may define both (1) a central lumen 136 that extends through the rotatable magazine 130 and (2) a plurality of chambers 131, 132, 133, 134, 135 disposed around the central lumen 136. The rotatable magazine 130 may be coupled to the frame 110 via the elongate shaft 124. The elongate shaft 124 may be coupled to the frame 110 and extend through the central lumen 136 of the rotatable magazine 130, thereby allowing the rotatable magazine 130 to rotate around the elongate shaft 124. In this manner, the rotatable magazine 130 may be rotated independent of both the frame 110 and the syringe 102. In some embodiments, the rotatable magazine 130 is substantially cylindrical in shape.

In the depicted embodiment, the rotatable magazine 130 includes a first chamber 131, a second chamber 132, a third chamber 133, a fourth chamber 134, and a fifth chamber 135. Rotatable magazines 130 that include more or less than five chambers are also within the scope of this disclosure. For example, in other embodiments, the rotatable magazine 130 may include two, three, four, six, seven, eight, nine, or 10 chambers.

Each chamber 131, 132, 133, 134, 135 may be configured to receive a composition or a medical article. For example, in some embodiments, each chamber 131, 132, 133, 134, 135 is configured to hold a medicament, such as a drug in powder form or microspheres. Exemplary medicaments include antimicrobials, anticoagulants, or any other drug. In some embodiments, the chambers 131, 132, 133, 134, 135 of the medical plug delivery device 100 are preloaded with a medicament. In some embodiments, each chamber 131, 132, 133, 134, 135 is configured to receive (and/or is preloaded with) a medical plug 140.

In some embodiments, a cartridge 160 is disposed within each of the chambers 131, 132, 133, 134, 135. The cartridges 160 may be generally elongate in shape with a hollow interior that defines a primary channel 162. Each cartridge 160 may be sized to accommodate a single composition or medical article (e.g., a medical plug 140). While the chamber 131 and the cartridge 160 are depicted as separate components, one of ordinary skill in the art, with the benefit of this disclosure, will recognize that the chamber 131 and the cartridge 160 may be combined into one integrally formed component in some embodiments. In other words, in some embodiments, the entire rotatable magazine 130 is an integrally formed monolithic part.

In some embodiments, the cartridge 160 fits within the chamber 131 via an interference fit. In other embodiments, the cartridge 160 is attached to the chamber 131 via an adhesive. In some embodiments, there is gap between at least a portion of the cartridge 160 and a portion of the chamber 131. The gap may be part of a bypass channel 164 that allows fluid to travel from the proximal end of the distal channel 148, around the exterior surface of the cartridge 160 to the proximal channel 147 of the frame 110 without passing through a medical plug 140 (or other composition) that is disposed within the primary channel 162 of the cartridge 160. In other words, the bypass channel 164 may provide a fluid flow path around the primary channel 162. However, in other embodiments, no bypass channel is available. Fluid flow in either direction (i.e., proximal to distal or distal to proximal) through the bypass channel 164 is within the scope of this disclosure.

The cartridge 160 may also include a shoulder 150 that is configured to restrict proximal displacement of a medical plug 140 during operation of the medical plug delivery device 100. In the depicted embodiment, the shoulder 150 is an annular protrusion that extends inward from the cartridge 160. The shoulder 150 may narrow a passageway (i.e., primary channel 162) through the cartridge 160. In other words, a proximal portion of the primary channel 162 (e.g., the portion defined by the shoulder 150) may have a smaller diameter than a distal portion of the primary channel 162. The one or more shoulders 150 may be disposed adjacent a proximal end of the chamber 131. The shoulder(s) 150 may be configured to restrict proximal displacement of a medical plug 140 during operation of the medical plug delivery device 100. Stated differently, the shoulder(s) 150 may be configured to engage a medical plug 140 and restrict movement of the medical plug 140 proximal of the shoulder 150.

The rotatable magazine 130 may include a ledge 137 adjacent a proximal end of the rotatable magazine 130. The ledge 137 may be designed to contact the cartridge 160, thereby preventing movement of the cartridge 160 past the ledge 137. Other embodiments may lack a ledge.

The rotatable magazine 130 may be disposed directly between the distal portion 118 and the proximal portion 116 of the frame 110. The distal portion 118 and the proximal portion 116 of the frame 110 may together provide a compressive force on the rotatable magazine 130 to form a fluid-tight seal between the frame 110 and a chamber of the plurality of chambers 131, 132, 133, 134, 135. More particularly, in some embodiments, the rotatable magazine 130 includes a proximal sloped surface 138 that is configured to mate with a corresponding surface (e.g., a first frustoconical protrusion 126) of frame 110. The rotatable magazine 130 may also include a distal sloped surface 139 that is configured to mate with a corresponding surface (e.g., a second frustoconical protrusion 128) of the frame 110. (In other embodiments, the position of the frustoconical protrusions and the corresponding surfaces may be switched such that the rotatable magazine includes the frustoconical protrusions, and the frame includes the sloped surfaces.) The interactions of the protrusions 126, 128 with the sloped surfaces 138, 139 may form fluid-tight seals that place the rotatable magazine 130 in fluid communication with the reservoir 107 of the syringe 102. In this manner, a fluid-tight seal may be accomplished without the use of an o-ring. Further disclosure regarding the interaction between the frustoconical protrusions 126, 128 and the sloped surfaces 138, 139 is described below.

Rotation of the rotatable magazine 130 about the elongate shaft 124 may cause the medical plug delivery device 100 to transition from a first configuration in which a chamber of the plurality of chambers 131, 132, 133, 134, 135 is aligned with both the proximal channel 147 and the distal channel 148 to a second configuration in which a different chamber of the plurality of chambers 131, 132, 133, 134, 135 is aligned with both the proximal channel 147 and the distal channel 148.

For example, when the frame 110 and the rotatable magazine 130 are positioned as shown in FIGS. 1-7, the first chamber 131 may be in fluid communication with the proximal channel 147 and the distal channel 148. As the rotatable magazine 130 is rotated approximately 72 degrees in the direction indicated in FIGS. 3 and 4, the second chamber 132 may align with the proximal channel 147 and the distal channel 148 of the frame 110. As the rotatable magazine 130 is further rotated an additional 72 degrees, the third chamber 133 may be aligned with the proximal channel 147 and the distal channel 148. In like manner, the rotatable magazine 130 may be further rotated in increments of 72 degrees to align the fourth chamber 134 and then the fifth chamber 135 with the proximal channel 147 and the distal channel 148. When the frame 110 and the rotatable magazine 130 are positioned such that none of the chambers 131, 132, 133, 134, 135 align with the proximal channel 147 and the distal channel 148 of the frame 110 (e.g., the chambers 131, 132, 133, 134, 135 are disposed at some intermediate position), the rotatable magazine 130 may not be in fluid communication with the reservoir 107 of the syringe 102.

In some embodiments, the rotatable magazine 130 is configured to hold a plurality of medical plugs 140. For example, a medical plug 140 may be disposed in each of chambers 131, 132, 133, 134, 135 of the rotatable magazine 130. More particularly, in some embodiments, a medical plug 140 may be disposed within a cartridge 160 that is disposed within the chamber 131 of the rotatable magazine 130. In some embodiments, the rotatable magazine 130 (or a portion thereof) is substantially transparent, thereby allowing the practitioner to visualize wetting and/or ejection of the medical plug 140 as described below. In other embodiments, the rotatable magazine 130 is opaque. In some embodiments, each medical plug 140 is a different length from other medical plugs 140 in the chambers 131, 132, 133, 134, 135 of the medical plug delivery device 100. For example, a first medical plug 140 having a first length may be disposed within the first chamber 131, while a second medical plug (not shown) having a second length (i.e., a length that differs from the first length) may be disposed within the second chamber 132. In this manner, the medical plug delivery device 100 may be used as a medical plug deployment device for selecting a medical plug 140 of appropriate length for a particular medical need from among the various lengths of the medical plugs 140 that are disposed within chambers 131, 132, 133, 134, 135 of the rotatable magazine 130. In some embodiments, indicia corresponding to the lengths of the medical plugs 140 may be disposed on the rotatable magazine 130.

The medical plugs 140 may be of any suitable composition, shape, and/or size. For example, in some embodiments, the medical plugs 140 include or consist essentially of a bioabsorbable material. In some embodiments, the bioabsorbable material (or a portion thereof) is derived from animal tissue, such as pig skin or cow skin. In some embodiments, the bioabsorbable material is a collagen-containing material, such as a gelatin foam from an animal source. In other or further embodiments, the bioabsorbable material (or a portion thereof) is a synthetic polymer, such as polylactic acid, polyglycolide, or poly(lactic-co-glycolic acid). In some embodiments, the medical plugs 140 include or consist of a non-bioabsorbable material, such as polyvinyl alcohol or polyvinyl acetate. In some embodiments, the medical plugs 140 include a dye. The dye may facilitate visualization of the medical plugs 140 when the medical plugs 140 are disposed within the rotatable magazine 130. In some embodiments, the medical plugs 140 may change colors when contacted with fluid (e.g., water or saline), thereby allowing a practitioner to visually determine when the medical plugs 140 have been wetted.

The medical plugs 140 may be generally elongate in shape. For example, in some embodiments, the medical plugs 140 are elongate pieces of material that have been rolled into a substantially cylindrical shape of between 1 mm and 5 mm (e.g., approximately 2 mm) in diameter. Each medical plug 140 may have a length that is at least two-fold, at least five-fold, and/or at least 10-fold longer than the diameter of the medical plug 140. In some embodiments, each medical plug 140 is between 10 mm and 70 mm in length. For example, in some embodiments, one or more medical plugs 140 are between 10 mm and 50 mm and/or between 10 mm and 40 mm (e.g., approximately 20 mm) in length.

The medical plug delivery device 100 may be used to deploy compositions or medical articles (e.g., medical plugs 140) to a patient. While processes are described below with particular reference to medical plugs 140, a skilled artisan with the benefit of this disclosure will recognize that analogous processes may be used to deploy other medical articles or compositions.

To wet and deploy a first medical plug 140 from the rotatable magazine 130, a practitioner may obtain a syringe 102 that includes a plunger 106. The practitioner may then attach the syringe 102 to the frame 110 (which is coupled to the rotatable magazine 130 via the elongate shaft 124). The plunger 106 may be initially disposed such that the plunger 106 abuts against the distal tip of the syringe 102. Liquid, such as water, saline, contrast, any mixture thereof, or any other fluid, may then be drawn into the medical plug delivery device 100 to wet the first medical plug 140 within a first chamber 131 and introduce fluid into the reservoir 107 of the syringe 102. For example, the plunger 106 may be retracted within the body of the syringe 102 while the distal end of the frame 110 is disposed within the liquid. As the plunger 106 is retracted in this manner, fluid may be drawn into the reservoir 107 of the syringe 102 via two different pathways. Stated another way, application of a negative pressure within the reservoir 107 may tend to draw fluid into the reservoir 107 via one or both fluid pathways further described below.

First, as the plunger 106 is retracted, fluid may be drawn into the distal channel 148, continue through the primary channel 162 (and thereby pass through and wet the medical plug 140), pass through the proximal channel 147, and then enter the reservoir 107 of the syringe 102. The shoulder 150 of the cartridge 160 may prevent proximal displacement of the medical plug 140 past the shoulder 150, thereby ensuring that the medical plug 140 is not inadvertently sucked into the reservoir 107 of the syringe 102. In other words, the shoulder 150 may engage with the medical plug 140 to inhibit or restrict proximal displacement of the medical plug 140. Wetting of the medical plug 140 may increase the lubricity of the medical plug 140, thereby facilitating both ejection of the medical plug 140 from the medical plug delivery device 100 and advancement of the medical plug 140 through a lumen of an elongate tube to an interior portion (e.g., a void) within a patient. In some embodiments, the medical plug 140 may also swell as it wets, and may thus partially occlude or disrupt fluid flow through the primary channel 162.

Second, instead of passing through the medical plug 140, fluid may be drawn into the distal channel 148, pass through the bypass channel 164, and travel proximally through the proximal channel 147 to enter into the reservoir 107 of the syringe 102. Fluid passing through this pathway bypasses the medical plug 140.

The two pathways described above may both operate to fill (or partially fill) the reservoir 107 of the syringe 102. For example, as the plunger 106 is initially retracted, fluid may primarily follow the first pathway (i.e., through the medical plug 140). In some embodiments, as fluid passes through the medical plug 140, the medical plug 140 is wetted. Wetting and swelling of the medical plug 140 may obstruct further fluid flow through the medical plug 140. As the flow rate of fluid through the medical plug 140 decreases, a greater proportion of the fluid may instead pass through the second pathway (i.e., through the bypass channel 164) to enter into the reservoir 107 of the syringe 102.

Relative flow rates between the two pathways may depend on a variety of factors, such as the composition of the medical plug 140 and the cross-sectional surface areas presented by the primary channel 162 and the bypass channel 164. For example, in some embodiments, the cross-sectional surface area of the primary channel 162 (where the cross-section is perpendicular to the longitudinal axis of the medical plug delivery device 100) is greater than the cross-sectional surface area of the bypass channel 164. Thus, a relatively large fluidic force may be applied to the medical plug 140 (during both retraction and advancement of the plunger 106) due to its positioning within a channel (i.e., the primary channel 162) having a relatively large cross-sectional surface area in comparison with the cross-sectional surface area of the bypass channel 164.

If desired, any air bubbles that were introduced into the medical plug delivery device 100 as the plunger 106 was retracted may be removed in the traditional manner (i.e., by orienting the medical plug delivery device 100 such that the distal end of the medical plug delivery device 100 is pointed upward, tapping the medical plug delivery device 100, and ejecting air bubbles by advancing the plunger 106 toward the distal end of the medical plug delivery device 100).

In some circumstances, once both (1) the medical plug 140 has been wetted, and (2) a sufficient quantity of fluid has entered into the reservoir 107 of the syringe 102, the practitioner may couple the distal end of the frame 110 to an elongate tube, such as an introducer sheath or catheter. The elongate tube may be in fluid communication with a void into which the medical plug 140 is to be inserted. For example, the distal adaptor 114 of the frame 110 may be coupled to a proximal end of an introducer sheath used in a biopsy procedure as described above. The practitioner may then advance the plunger 106 toward the distal end of the syringe 102, thereby displacing fluid in a distal direction.

As the fluid is displaced in a distal direction, the fluid may be expelled from the syringe 102, travel through the proximal channel 147 of the frame 110, and exert a distal force on the medical plug 140 disposed therein, thereby causing distal displacement and ejection of the medical plug 140 from the rotatable magazine 130. The medical plug 140 may then continue onward, travelling through the distal channel 148 of the frame 110, and through an elongate tube that is coupled to the frame 110 to be placed within a void of the patient. The inserted medical plug 140 may serve any suitable purpose, such as obstructing fluid flow, inducing blood coagulation, and/or providing a scaffold to promote tissue growth.

In some embodiments or circumstances, instead of retracting the plunger 106 to draw fluid into the reservoir 107 of the syringe 102 as described above, the syringe 102 may be pre-filled with liquid. The distal end of the pre-filled syringe 102 may then be attached to a proximal end of the frame 110. Once the syringe 102 is attached to the proximal end of the frame 110, the plunger 106 may be advanced. Advancement of the plunger 106 in this manner may both wet the particular medical plug 140 and discharge the medical plug 140 from the medical plug delivery device 100 into an elongate tube for delivery to a void as described above. In other words, medical plugs 140 may be hydrated as they are ejected from the rotatable magazine 130 instead of being wetted by retraction of the plunger 106.

Once the first medical plug 140 has been deployed from the first chamber 131, the medical plug delivery device 100 may be transitioned to a different configuration in which the second chamber 132 is in fluid communication with the distal channel 148 of the frame 110. To transition the medical plug delivery device 100 to this configuration, the practitioner may apply a rotational force to the rotatable magazine 130, thereby causing the rotatable magazine 130 to be rotationally displaced relative to the frame 110. Such rotational displacement of the rotatable magazine 130 with respect to the frame 110 may cause a transition from a first configuration in which the first chamber 131 is in fluid communication with the distal channel 148 to a second configuration in which a second chamber 132 is in fluid communication with the distal channel 148 of the frame 110.

As the rotatable magazine 130 is initially rotated, the first frustoconical protrusion 126 may slide along the sloped surface 138 of the rotatable magazine 130, thereby disrupting the fluid-tight seal between the first frustoconical protrusion 126 and the sloped surface 138. At the same time, the second frustoconical protrusion 128 may slide along the sloped surface 139 of the rotatable magazine 130, thereby disrupting the fluid-tight seal between the second frustoconical protrusion 128 and the sloped surface 139.

In some embodiments, as the rotatable magazine 130 is initially rotated from a position in which the first chamber 131 is aligned with both the proximal channel 147 and the distal channel 148 of the frame 110, the frame 110 may flex, causing an increase in displacement between the proximal portion 116 of the frame 110 and the distal portion 118 of the frame 110. For example, due to the notches 142 in the frame 110, the frame 110 may bend, deflect, and/or flex about one or more flex points 144, thereby causing an increase in displacement between the proximal portion 116 of the frame 110 and the distal portion 118 of the frame 110. In some embodiments, the frame 110 is designed to flex in a single plane (i.e., the plane defining the cross-section shown in FIG. 5). In some embodiments, a free end of the proximal portion 116 may bend further away from the distal portion 118 than other regions of the proximal portion 116. The cavity 146 of the frame 110 may be designed (e.g., be elongate in shape) to accommodate any displacement of the elongate shaft 124 within the cavity 146 that occurs as the frame 110 is bent while the medical plug delivery device 100 transitions from a first configuration in which the first chamber 131 is aligned with both the proximal channel 147 and the distal channel 148 to a second configuration in which the second chamber 132 is aligned with both the proximal channel 147 and the distal channel 148. Stated differently, the cavity 146 may provide clearance for the elongate shaft 124, thereby allowing the frame 110 to flex.

As the rotatable magazine 130 is further rotated, the first frustoconical protrusion 126 may approach a proximal opening to the second chamber 132, and the second frustoconical protrusion 128 may approach a distal opening to the second chamber 132. As the first frustoconical protrusion 126 and the second frustoconical protrusion 128 approach the second chamber 132, the frame 110 may exert a compressive force on the rotatable magazine 130 due to the resiliency of the frame 110. Stated differently, the frame 110 may be biased to provide a compressive force when in a flexed state. Such a compressive force may cause the first frustoconical protrusion 126 to slide along the sloped surface 138 adjacent the second chamber 132, and the second frustoconical protrusion 128 to slide along the sloped surface 139 such that the frustoconical protrusions 126, 128 are guided to a position in which the second chamber 132 is aligned with the proximal channel 147 and the distal channel 148 of the frame 110. When aligned in this manner, the frustoconical protrusions 126, 128 and the sloped surfaces 138, 139 may form liquid-tight seals. In other words, the compressive force provided by the frame 110 may facilitate seating of the frustoconical protrusions 126, 128 into the corresponding sloped surfaces 138, 139.

In some embodiments, the compressive force may cause the frustoconical protrusions 126, 128 to snap into the sloped surfaces 138, 139, thereby providing the practitioner with tactile and/or audible feedback that one of the chambers 131, 132, 133, 134, 135 is properly aligned with the proximal channel 147 and the distal channel 148 of the frame 110. In some embodiments, the frame 110 and/or the rotatable magazine 130 include indicia that allow the practitioner to visually determine whether the proximal channel 147 and the distal channel 148 are aligned with a particular chamber 131, 132, 133, 134, 135 of the rotatable magazine 130.

Once the frame 110 and the rotatable magazine 130 are positioned such that the second chamber 132 of the rotatable magazine 130 is aligned with both the proximal channel 147 and the distal channel 148, the practitioner may wet and deploy a second medical plug 140 from the second chamber 132 in a manner analogous to that described above in connection with the first medical plug 140 that was disposed within the first chamber 131. Once the second medical plug 140 has been deployed, the rotatable magazine 130 may be further rotated relative to the frame 110 to enable wetting and deployment of a third medical plug 140 from the third chamber 133. Medical plugs within the fourth chamber 134 and the fifth chamber 135 may be wetted and deployed by analogous methods. A skilled artisan will recognize that rotatable magazines 130 that include any number of medical plugs 140 are contemplated and within the scope of this disclosure.

In some embodiments, the rotatable magazine 130 may be rotated while using only a single hand. For example, when the syringe 102 is held between the palm of the hand and the middle, ring, and/or pinky fingers, the rotatable magazine 130 may be rotated between the thumb and index finger of the same hand. In some embodiments, such as the embodiment depicted in FIGS. 1-7, the medical plug delivery device 100 is configured for ambidextrous use. In other words, the medical plug delivery device 100 may be principally or exclusively operated using either the left hand or the right hand.

In the depicted embodiment, the medical plug delivery device 100 is configured to rotate in either a counterclockwise or a clockwise direction (as viewed from the distal end of the medical plug delivery device 100). In other embodiments, the medical plug delivery device 100 is configured to rotate around the elongate shaft 124 in only a single direction. Further, in some embodiments, the medical plug delivery device 100 may include a stop (e.g., an obstruction) (not shown) that prevents more than one rotation of the rotatable magazine 130 about the elongate shaft 124. Embodiments that both (1) permit only unidirectional rotation of the rotatable magazine 130 and (2) include a stop such as the stop described above may prevent a practitioner from unintentionally returning to a chamber 131, 132, 133, 134, 135 from which a composition or medical article has already been deployed.

The medical plug delivery device 100 may be manufactured via any suitable method. For example, in some embodiments, a method of manufacturing the medical plug delivery device 100 comprises placing the rotatable magazine 130 between the proximal portion 116 and the distal portion 118 of the frame 110. Adhesive may then be placed along the edges of a cavity in the distal portion 118 of the frame 110. The elongate shaft 124 may then be inserted through the (proximal) cavity 146, through the central lumen 136 of the rotatable magazine 130, and into the (distal) cavity such that the adhesive binds to a distal end of the elongate shaft 124. In this manner, the distal end of the elongate shaft 124 (but not the proximal end) is attached to the frame 110. In some embodiments, manufacture of the rotatable magazine 130 involves insertion of a plurality of cartridges 160 into the chambers 131, 132, 133, 134, 135 of the rotatable magazine 130. Each of the cartridges 160 may be attached to one of the chambers 131, 132, 133, 134, 135 via an adhesive.

Figure 8:
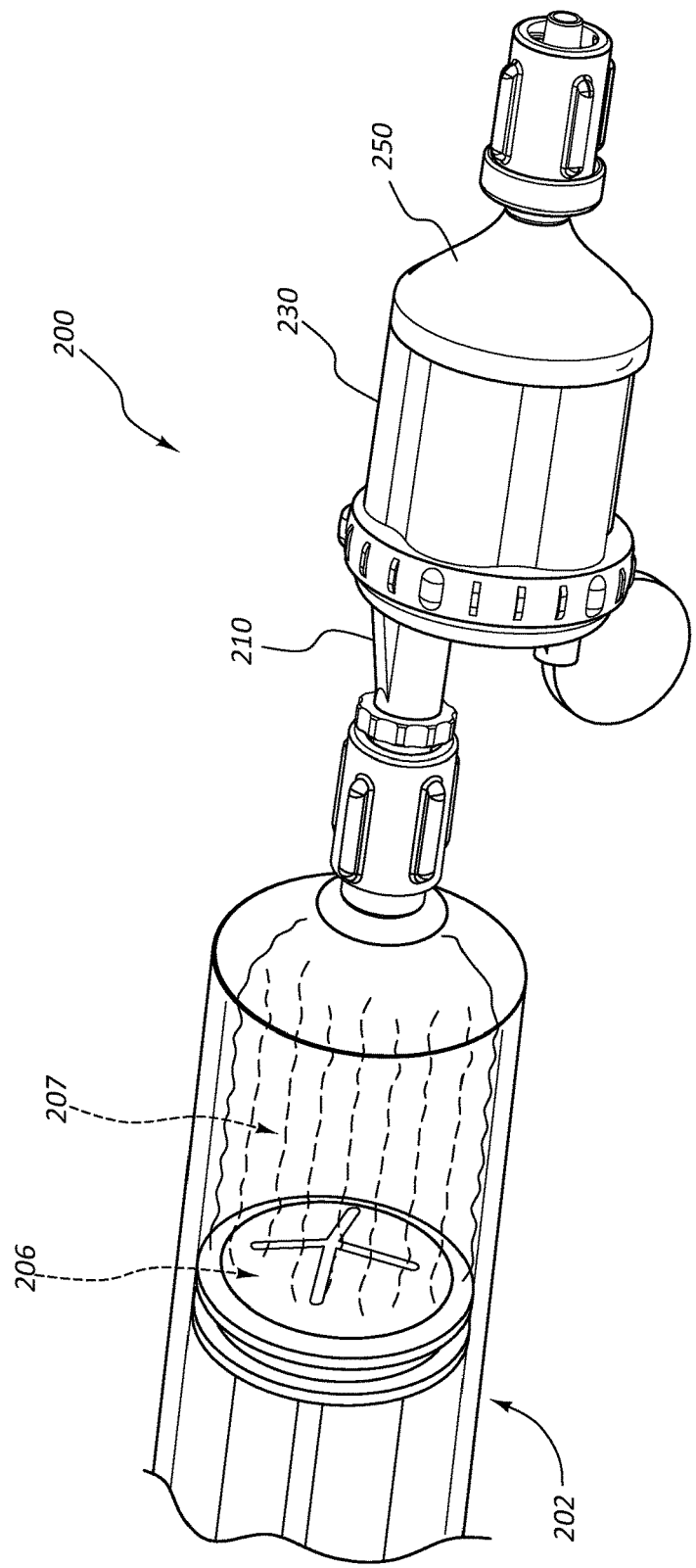
FIG. 8 is a perspective view of another embodiment of a medical plug delivery device.
Figure 9:
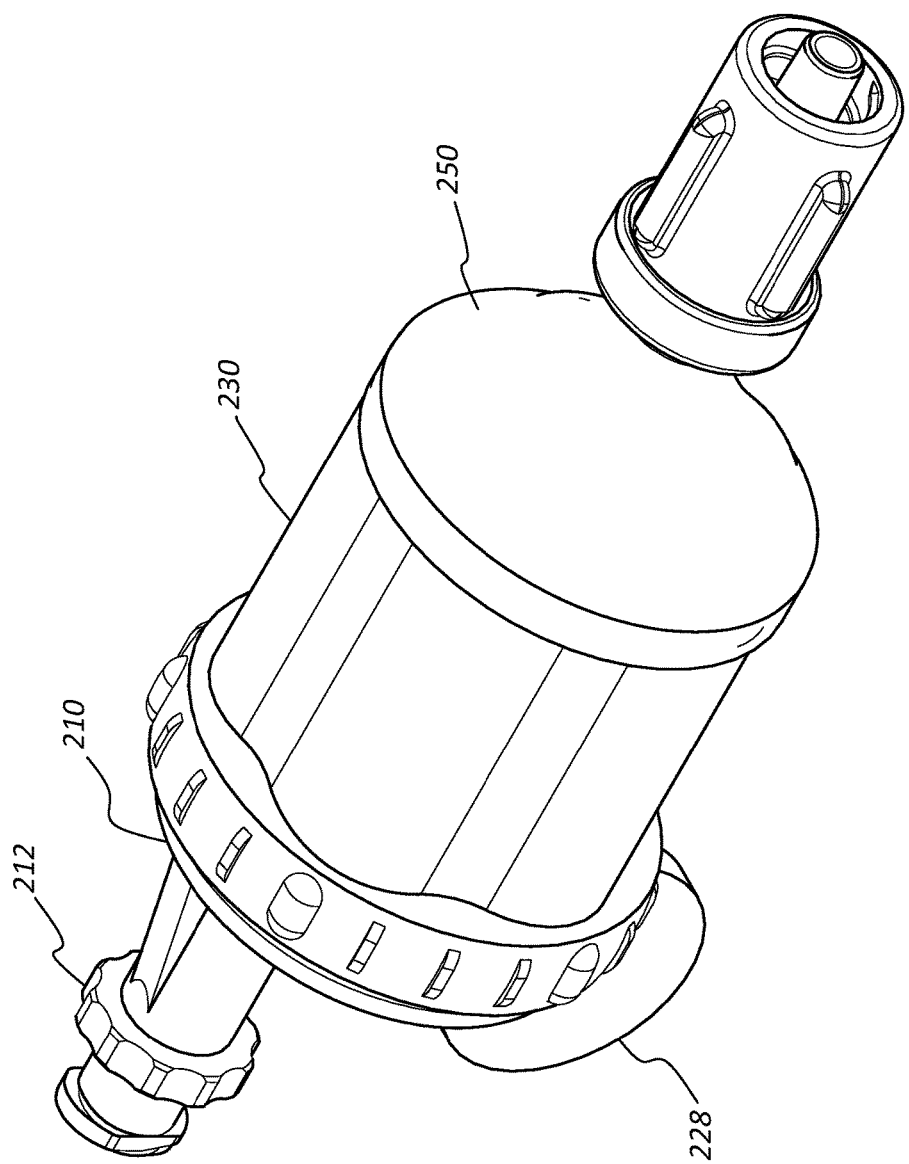
FIG. 9 is another perspective view of the medical plug delivery device of FIG. 8, with the syringe removed for clarity.
Figure 10:
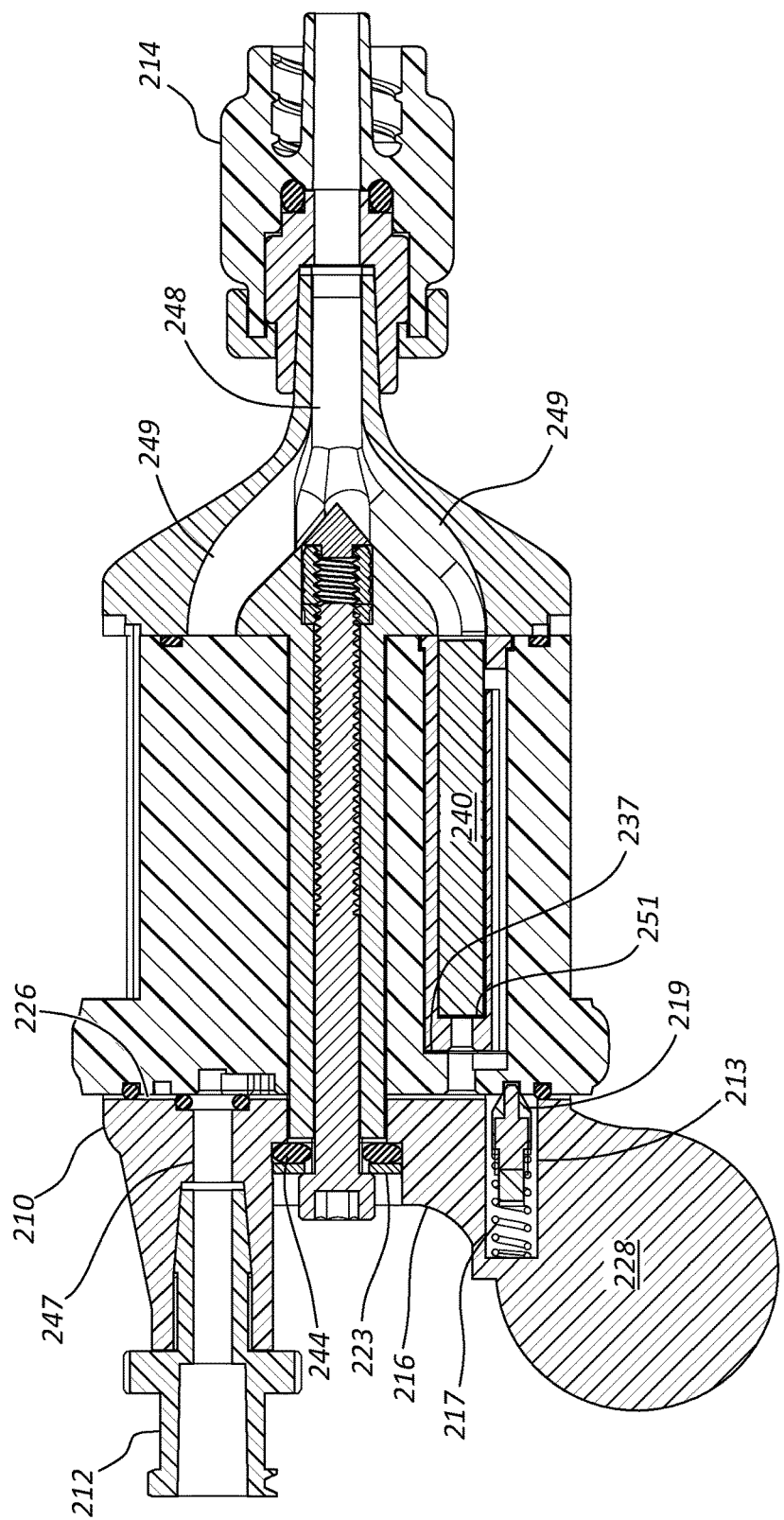
FIG. 10 is a cross-sectional view of a portion of the medical plug delivery device of FIGS. 8-9.
Figure 11:
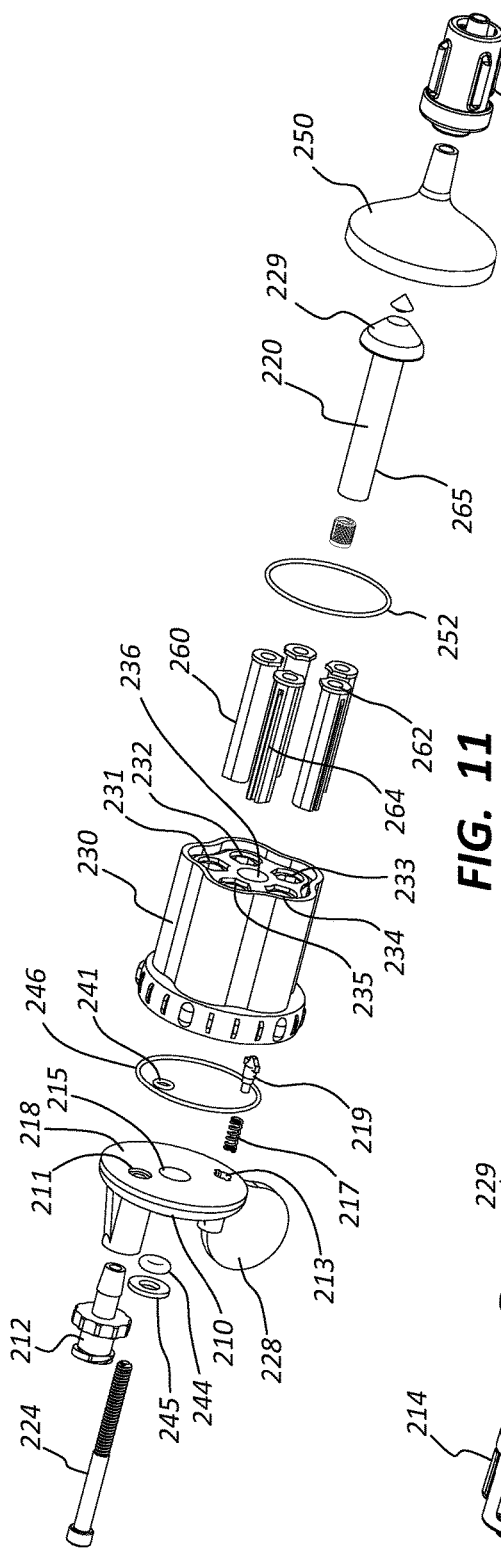
FIG. 11 is an exploded view of a portion of the medical plug delivery device of FIGS. 8-10.
Figure 12:
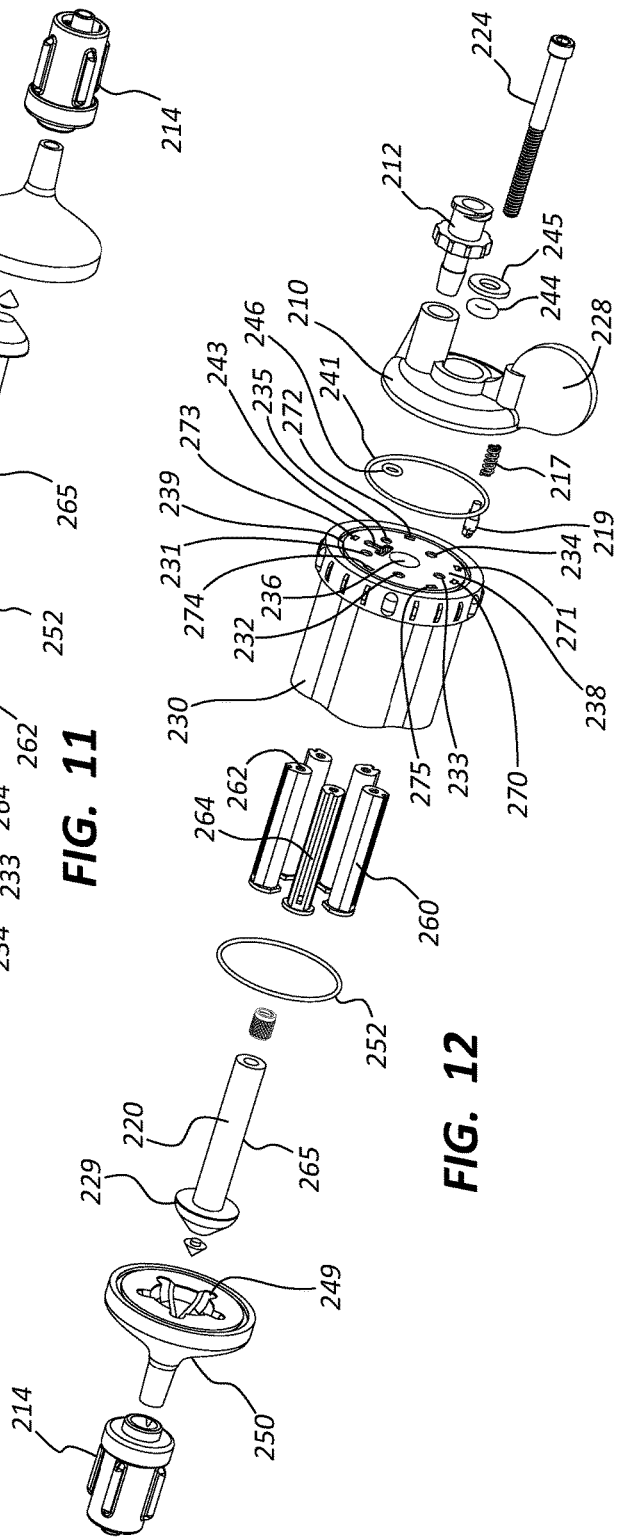
FIG. 12 is another exploded view of a portion of the medical plug delivery device of FIGS. 8-11.

FIGS. 8-14 depict a medical plug delivery device 200 (or portions thereof) for delivering compositions and/or medical articles to a patient. More particularly, FIG. 8 provides a perspective view of the medical plug delivery device 200. FIG. 9 provides an alternative perspective view of the medical plug delivery device 200, with a syringe 202 removed for clarity. FIG. 10 is a cross-sectional view of a portion of the medical plug delivery device of FIGS. 8-9. FIG. 11 is an exploded view of a portion of the medical plug delivery device. FIG. 12 is another exploded view of a portion of the medical plug delivery device. FIG. 13 is a proximal end view of the medical plug delivery device with the selector in a first position. FIG. 14 is a proximal end view of the medical plug delivery device with the selector in a second position.

As depicted in FIGS. 8-14, the medical plug delivery device 200 may include a fluid delivery device such as the syringe 202, a selector 210, a guide 250, and a magazine 230.

The syringe 202 may include a plunger 206 that is configured to be at least partially disposed within the body of the syringe 202 such that advancement and retraction of the plunger 206 causes displacement of fluid within a reservoir 207 of the syringe 202. The syringe 202 may be configured to couple to a proximal end of the selector 210. For example, in the depicted embodiment, the syringe 202 includes a male Luer lock connector 208 at its distal end. In some embodiments, the syringe 202 is a standard, commercially available syringe. The syringe 202 may be capable of holding enough fluid to facilitate deployment of multiple medical compositions or articles (e.g., medicaments or medical plugs 240) into a patient. For example, in some embodiments, the syringe 202 is capable of holding at least 3 mL, at least 5 mL, at least 10 mL and/or at least 15 mL of fluid. In some embodiments, the syringe 202 may be a vacuum lock syringe that allows practitioners to lock the plunger 206 at multiple positions along the body of the syringe 202. In other embodiments, the syringe 202 does not include a vacuum lock.

The selector 210 may include a proximal portion 216 and a distal surface 218. The proximal portion 216 may include a proximal adaptor 212, a proximal channel 247 and a rotation tab 228. The distal surface 218 may include a distal end 211 of the channel 247, an elastic member recess 213, and an orifice or through hole 215.

The proximal adaptor 212 may be configured to couple to the distal end of the syringe 202. For example, in the depicted embodiment, the proximal adaptor 212 of the selector 210 is a female Luer connection that is designed to couple to (e.g., form a fluid-tight connection with) the male Luer connection at the distal end of the syringe 202.

The proximal channel 247 and a distal channel 248 may be configured to provide portions of a fluid flow path. The fluid flow path may allow fluid to flow sequentially from the reservoir 207 of the syringe 202 to the proximal channel 247, from the proximal channel 247 to a first chamber 231 of the magazine 230, from the chamber 231 of the magazine 230 to the distal channel 248, and from the distal channel 248 to the patient. The fluid flow path may also allow fluid flow in the reverse direction, i.e., from the distal channel 248, through the chamber 231 of the magazine 230, through the proximal channel 247 to the reservoir 207 of the syringe 202.

In the depicted embodiment, the proximal channel 247 and the distal channel 248 are not co-linear with one another, such that the proximal channel 247 may be radially offset from the longitudinal axis of the medical plug delivery device 200, and the distal channel 248 may be centrally aligned with the longitudinal axis of the medical plug delivery device 200. In some embodiments, the longitudinal axis of the medical plug delivery device 200 may not pass through the center of gravity. Rather, the center of gravity may be radially displaced.

The selector 210 may include a rotation tab 228 configured to allow the practitioner to rotate the selector 210 relative to the magazine 230. The rotation tab 228 may be radially offset and extend proximally from the proximal portion 216 of the selector 210. The rotation tab 228 may be positioned approximately 180 degrees from the proximal channel 247. The rotation tab 228 may be configured to allow the practitioner to apply a rotational force to the rotation tab 228 with a finger or thumb or to grip the rotation tab 228 between a finger and thumb to apply a rotational force.

The elastic member recess 213 of the distal surface 218 of the selector 210 may be configured to retain an elastic member 217 and a detent 219. The elastic member recess 213 may be radially disposed toward the outer perimeter of the distal surface 218 and approximately 180 degrees from the distal end 211 of the proximal channel 247. The elastic member 217 may be any type of elastically deformable member, such as a coiled spring, leaf spring, leaf arm, etc. The elastic member 217 may be configured to be compressed or biased and to provide a directed force to the detent 219. The detent 219 may engage the elastic member 217 and may be at least partially retained by the elastic member recess 213. The distal end of the detent 219 may include a square side 221 and a sloped side 222 that is opposite of the square side 221.

In some embodiments, the distal surface 218 of the selector 210 may face a proximal surface 238 of the magazine 230. The proximal surface 238 may include an annular recess 239 near the perimeter of the proximal surface 238. The annular recess 239 may be configured for retention of a perimeter sealing member 241. The perimeter sealing member 241 may be an o-ring or other similar type of sealing device. The proximal surface 238 may also include recesses 270, 271, 272, 273, 274, 275 disposed near the annular recess 239. Each of the recesses 270, 271, 272, 273, 274, 275 may be configured to define a position where the proximal channel 247 is either not in alignment with proximal ends 242 of the chambers 231, 232, 233, 234, 235 or in alignment with the proximal ends 242 of the chambers 231, 232, 233, 234, 235. The number of recesses 270, 271, 272, 273, 274, 275 may equal the number of chambers 231, 232, 233, 234, 235 plus one additional recess 270, 271, 272, 273, 274, 275. For example, in one embodiment, if the number of chambers 231, 232, 233, 234, 235 is five then the number of recesses 270, 271, 272, 273, 274, 275 is six. The recesses 270, 271, 272, 273, 274, 275 may be configured to interface with the detent 219. The recesses 270, 271, 272, 273, 274, 275 may be configured with a sloped side and a square face (or otherwise non-sloped side) to correspond to the sloped face and square side (or non-sloped side) of the detent 219. The interface between the detent 219 and the recesses 270, 271, 272, 273, 274, 275 may define rotation of the selector 210 in only one direction. For example, the square side of the detent 219 may face the square side of the recess 270, 271, 272, 273, 274, 275 and prevent rotation of the selector 210 when the two square sides are forced against one another.

Rotation is possible when the sloped side of the detent 219 faces the sloped side of the recess 270, 271, 272, 273, 274, 275 and a force is applied against the two sloped sides.

The proximal surface 238 further defines a cavity 243. The cavity 243 may be positioned between two proximal ends 242 of the chambers 231, 232, 233, 234, 235. For example, in one embodiment the cavity 243 may be positioned between the first chamber 231 and a fifth chamber 235. The cavity 243 may be "T" shaped with the leg of the "T" directed to the perimeter of the proximal surface 218. In some embodiments, the distal surface 218 may comprise the recess 270, 271, 272, 273, 274, 275, and the proximal surface 238 of the magazine 230 may comprise the elastic member recess 213.

A gap 226 may be defined between the distal surface 218 of the selector 210 and the proximal surface 238 of magazine 230. The gap 226 may be sealed on its perimeter by the perimeter sealing member 241 and near its center by an elongate member o-ring 244 surrounding the elongate member 224. A spacer disc 245 surrounding the elongate member 224 may be configured to prevent the proximal surface 238 and the distal surface 218 from touching, thus providing the gap 226. A distal end o-ring 246 may be positioned at the distal end 211 of the proximal channel 247. The distal end o-ring 246 may be configured to direct fluid flow either from the proximal channel 247 to a chamber 231, 232, 233, 234, 235 or from a chamber 231, 232, 233, 234, 235 to the proximal channel 247 when the proximal channel 247 is in alignment with the chamber 231, 232, 233, 234, 235. Therefore, fluid is selectively directed into or from a chamber 231, 232, 233, 234, 235. Alternatively, the proximal channel 247 may be in alignment with the cavity 243. In this position, the distal end o-ring 246 does not prevent fluid from flowing into the gap 226. Rather, fluid is permitted to flow either from the proximal channel 247, through the cavity 243, into the gap 226, and simultaneously into the chambers 231, 232, 233, 234, 235, or from the chambers 231, 232, 233, 234, 235, into the gap 226, through the cavity 243 and into the proximal channel 247. In other words, the gap 226 is configured to allow for simultaneous fluid flow to all of the chambers 231, 232, 233, 234, 235 from the proximal channel 247 or to allow for simultaneous flow from all of the chambers 231, 232, 233, 234, 235 to the proximal channel 247.

The guide 250 may include the distal channel 248 and guide channels 249. The proximal ends of the guide channels 249 may align with the chambers 231, 232, 233, 234, 235. The guide channels 249 may merge into the distal channel 248. The guide channels 249 are configured either to guide or direct fluid flow into the chambers 231, 232, 233, 234, 235 from the distal channel 248 or to direct or guide fluid flow and/or the medical plug 240 into the distal channel 248. The guide 250 may be generally cone shaped and be configured to be attached to the distal end of the magazine 230. The distal channel 248 may include a distal adaptor 214 that is configured to couple to an elongate tube, such as an introducer sheath or catheter that is in fluid communication with an interior of a patient. In some embodiments, the distal adaptor 214 is a simple male Luer connection. Such a simple connection may be formed integrally with the guide 250. In other embodiments, the distal adaptor 214 includes a male Luer lock connection that is configured to rotate independent of the remainder of the guide 250.

The magazine 230 may define both a central lumen 236 that extends through the magazine 230 and a plurality of chambers 231, 232, 233, 234, 235 disposed around the central lumen 236. A shouldered cylinder 220 may be partially disposed within the central lumen 236. The shouldered cylinder 220 may include a cylinder body 265 with a frustoconical shaped distal end 229 and a proximally directed shoulder 227. The magazine 230 may be fixedly and sealingly coupled to the guide 250 with a guide sealing member 252 positioned between the magazine 230 and the guide 250. The guide sealing member 252 may be an o-ring or other similar type of sealing device. Alternatively, the guide sealing member 252 may be excluded from the assembly.

The selector 210 may rotatably coupled to the magazine 230 (or the magazine 230 is rotatably coupled to the selector 210) via the elongate member 224. The body 265 of shouldered cylinder 220 may be disposed within the central lumen 236 with the shoulder 227 directed toward the distal end of the magazine 230. The elongate member 224 may extend through a rotation washer 223, through the through hole 216 of the selector 210, through the spacer disc 245, through the elongate member o-ring 244 and into the body 265 of shouldered cylinder 220. The elongate member 224 may be threadably coupled to the shouldered cylinder 220 such that as the elongate member 224 is threaded into the shouldered cylinder 220, the shoulder 227 contacts the distal face of the magazine 230. The head of the elongate member 224 and the shoulder 227 direct a compressive force to the selector 210 and the magazine 230 such that the distal surface 218 approximates the proximal surface 238 to provide the gap 226. The perimeter sealing member 241 may be compressed between the selector 210 and the magazine 230 to provide a fluid-tight seal. The selector 210 may be configured to rotate around the elongate member 224 relative to the magazine 230 while maintaining a fluid seal to the exterior of the medical plug delivery device 200. In some embodiments, the magazine 230 is substantially cylindrical in shape.

In the depicted embodiment, the magazine 230 includes a first chamber 231, a second chamber 232, a third chamber 233, a fourth chamber 234, and a fifth chamber 235. Magazines 230 that include more or less than five chambers are also within the scope of this disclosure. For example, in other embodiments, the magazine 230 may include two, three, four, six, seven, eight, nine, or 10 chambers.

Each chamber 231, 232, 233, 234, 235 may be configured to receive a composition or a medical article. For example, in some embodiments, each chamber 231, 232, 233, 234, 235 is configured to hold a medicament, such as a drug in powder form or microspheres. Exemplary medicaments include antimicrobials, anticoagulants, or any other drug. In some embodiments, the chambers 231, 232, 233, 234, 235 of the medical plug delivery device 200 are preloaded with a medicament. In some embodiments, each chamber 231, 232, 233, 234, 235 is configured to receive (and/or is preloaded with) a medical plug 240.

In some embodiments, a cartridge 260 is disposed within each of the chambers 231, 232, 233, 234, 235. The cartridges 260 may be generally elongate in shape with a hollow interior that defines a primary channel 262. Each cartridge 260 may be sized to accommodate a single composition or medical article (e.g., a medical plug 240). While the chamber 231 and the cartridge 260 are depicted as separate components, one of ordinary skill in the art, with the benefit of this disclosure, will recognize that the chamber 231 and the cartridge 260 may be combined into one integrally formed component in some embodiments. In other words, in some embodiments, the entire magazine 230 is an integrally formed monolithic part.

In some embodiments, the cartridge 260 fits within the chamber 231 via an interference fit. In other embodiments, the cartridge 260 is attached to the chamber 231 via an adhesive. In some embodiments, there is gap between at least a portion of the cartridge 260 and a portion of the chamber 231. The gap may be part of a bypass channel 264 that allows fluid to travel from the proximal end of the distal channel 248, around the exterior surface of the cartridge 260 to the proximal channel 247 of the selector 210 without passing through a medical plug 240 (or other composition) that is disposed within a primary channel 262 of the cartridge 260. In other words, the bypass channel 264 may provide a fluid flow path around the primary channel 262. However, in other embodiments, no bypass channel is available. Fluid flow in either direction (i.e., proximal to distal or distal to proximal) through the bypass channel 264 is within the scope of this disclosure.

The cartridge 260 may also include a shoulder 251 that is configured to restrict proximal displacement of a medical plug 240 during operation of the medical plug delivery device 200. In the depicted embodiment, the shoulder 251 is an annular protrusion that extends inward from the cartridge 260. The shoulder 251 may narrow a passageway (i.e., primary channel 262) through the cartridge 260. In other words, a proximal portion of the primary channel 262 (e.g., the portion defined by the shoulder 251) may have a smaller diameter than a distal portion of the primary channel 262. One or more shoulders 251 may be disposed adjacent a proximal end of the chamber 231. The shoulder(s) 251 may be configured to restrict proximal displacement of a medical plug 240 during operation of the medical plug delivery device 200. Stated differently, the shoulder(s) 251 may be configured to engage a medical plug 240 and restrict movement of the medical plug 240 proximal of the shoulder 251.

The magazine 230 may include a ledge 237 adjacent a proximal end of the magazine 230. The ledge 237 may be designed to contact the cartridge 260, thereby preventing movement of the cartridge 260 past the ledge 237. Other embodiments may lack a ledge.

Rotation of the selector 210 about the elongate member 224 may cause the medical plug delivery device 200 to transition from a first configuration in which a chamber of the plurality of chambers 231, 232, 233, 234, 235 is not aligned with the proximal channel 247 to a second configuration in which a chamber of the plurality of chambers 231, 232, 233, 234, 235 is aligned with the proximal channel 247.

For example, when the selector 210 and the magazine 230 are positioned as shown in FIG. 13, the proximal channel 247 may be in fluid communication with the gap 226 through the cavity 243. As the selector 210 is rotated approximately 36 degrees in the direction indicated in FIG. 14, the detent 219 may disengage from the recess 270 and then engage with the recess 271. The first chamber 231 may align with and be in fluid communication with the proximal channel 247. As the selector 210 is rotated approximately 72 degrees, the detent 219 may disengage from the recess 271 and then engage with the recess 272. The second chamber 232 may align with and be in fluid communication with the proximal channel 247. As the selector 210 is rotated another approximately 72 degrees, the detent 219 may disengage from the recess 272 and then engage with the recess 273. The third chamber 233 may align with and be in fluid communication with the proximal channel 247. In like manner, the magazine 230 may be further rotated in increments of 72 degrees to align the fourth chamber 234 and then the fifth chamber 235 with the proximal channel 247.

In some embodiments, the force of the elastic member 217 on the detent 219 may cause the detent 219 to snap into the recesses 271, 272, 273, 274, 275 as the selector 210 is being rotated, thereby providing the practitioner with tactile and/or audible feedback that one of the chambers 231, 232, 233, 234, 235 is properly aligned with the proximal channel 247 and the distal surface of the selector 210. In some embodiments, the selector 210 and/or the magazine 230 include indicia that allow the practitioner to visually determine whether the proximal channel 247 is aligned with a particular chamber 231, 232, 233, 234, 235 of the magazine 230.

In some embodiments, the magazine 230 is configured to hold a plurality of medical plugs 240. For example, a medical plug 240 may be disposed in each of the chambers 231, 232, 233, 234, 235 of the magazine 230. More particularly, in some embodiments, a medical plug 240 may be disposed within a cartridge 260 that is disposed within the chamber 231 of the magazine 230. In some embodiments, the magazine 230 (or a portion thereof) is substantially transparent, thereby allowing the practitioner to visualize wetting and/or ejection of the medical plug 240 as described below. In other embodiments, the magazine 230 is opaque. In some embodiments, each medical plug 240 is a different length from the other medical plugs 240 in the chambers 231, 232, 233, 234, 235 of the medical plug delivery device 200. For example, a first medical plug 240 having a first length may be disposed within the first chamber 231, while a second medical plug (not shown) having a second length (i.e., a length that differs from the first length) may be disposed within the second chamber 232. In this manner, the medical plug delivery device 200 may be used as a medical plug deployment device for selecting a medical plug 240 of appropriate length for a particular medical need from among the various lengths of the medical plugs 240 that are disposed within the chambers 231, 232, 233, 234, 235 of the magazine 230. In some embodiments, indicia corresponding to the lengths of the medical plugs 240 may be disposed on the magazine 230.

The medical plugs 240 may be of any suitable composition, shape, and/or size. For example, in some embodiments, the medical plugs 240 include or consist essentially of a bioabsorbable material. In some embodiments, the bioabsorbable material (or a portion thereof) is derived from animal tissue, such as pig skin or cow skin. In some embodiments, the bioabsorbable material is a collagen-containing material, such as a gelatin foam from an animal source. In other or further embodiments, the bioabsorbable material (or a portion thereof) is a synthetic polymer, such as polylactic acid, polyglycolide, or poly(lactic-co-glycolic acid). In some embodiments, the medical plugs 240 include or consist of a non-bioabsorbable material, such as polyvinyl alcohol or polyvinyl acetate. In some embodiments, the medical plugs 140 include a dye. The dye may facilitate visualization of the medical plugs 140 when the medical plugs 240 are disposed within the magazine 230. In some embodiments, the medical plugs 240 may change colors when contacted with fluid (e.g., water or saline), thereby allowing a practitioner to visually determine when the medical plugs 140 have been wetted.

The medical plugs 240 may be generally elongate in shape. For example, in some embodiments, the medical plugs 240 are elongate pieces of material that have been rolled into a substantially cylindrical shape of between 1 mm and 5 mm (e.g., approximately 2 mm) in diameter. Each medical plug 240 may have a length that is at least two-fold, at least five-fold, and/or at least 10-fold longer than the diameter of the medical plug 240. In some embodiments, each medical plug 240 is between 10 mm and 70 mm in length. For example, in some embodiments, one or more medical plugs 240 are between 10 mm and 50 mm and/or between 10 mm and 40 mm (e.g., approximately 20 mm) in length.

The medical plug delivery device 200 may be used to deploy compositions or medical articles (e.g., medical plugs 240) to a patient. While processes are described below with particular reference to medical plugs 240, a skilled artisan with the benefit of this disclosure will recognize that analogous processes may be used to deploy other medical articles or compositions.

To wet and deploy a first medical plug 240 from the magazine 230, a practitioner may obtain a syringe 202 that includes a plunger 206. The practitioner may then attach the syringe 202 to the selector 210 (which is coupled to the magazine 230 via the elongate member 224). The plunger 206 may be initially disposed such that the plunger 206 abuts against the distal tip of the syringe 202. Liquid, such as water, saline, contrast, any mixture thereof, or any other fluid, may then be drawn into the medical plug delivery device 200 to wet the medical plugs 240 within the chambers 231, 232, 233, 234, 235 simultaneously and introduce fluid into the reservoir 207 of the syringe 202. For example, the plunger 206 may be retracted within the body of the syringe 202 while the distal channel 248 is disposed within the liquid. As the plunger 206 is retracted in this manner, fluid may be drawn into the reservoir 207 of the syringe 202 via two different pathways. Stated another way, application of a negative pressure within the reservoir 207 may tend to draw fluid into the reservoir 207 via one or both fluid pathways further described below.

First, as the plunger 206 is retracted, fluid may be drawn into the distal channel 248, simultaneously continue through the primary channels 262 of cartridges 260 (and thereby pass through and wet the medical plugs 240), pass through the gap 226, pass through the proximal channel 247, and then enter the reservoir 207 of the syringe 202. The shoulder 251 of the cartridge 260 may prevent proximal displacement of the medical plug 240 past the shoulder 251, thereby ensuring that the medical plug 240 is not inadvertently sucked into the reservoir 207 of the syringe 202. In other words, the shoulder 251 may engage with the medical plug 240 to inhibit or restrict proximal displacement of the medical plug 240. Wetting of the medical plug 240 may increase the lubricity of the medical plug 240, thereby facilitating both ejection of the medical plug 240 from the medical plug delivery device 200 and advancement of the medical plug 240 through a lumen of an elongate tube to an interior portion (e.g., a void) within a patient. In some embodiments, the medical plug 240 may also swell as it wets, and may thus partially occlude or disrupt fluid flow through the primary channel 262.

Second, instead of passing through the medical plug 240, fluid may be drawn into the distal channel 248, simultaneously pass through the bypass channels 264 of cartridges 260, travel proximally through the gap 226, and travel through the proximal channel 247 to enter into the reservoir 207 of the syringe 202. Fluid passing through this pathway bypasses the medical plug 240.

The two pathways described above may both operate to fill (or partially fill) the reservoir 207 of the syringe 202. For example, as the plunger 206 is initially retracted, fluid may primarily follow the first pathway (i.e., through the medical plug 240). In some embodiments, as fluid passes through the medical plug 240, the medical plug 240 is wetted. Wetting and swelling of the medical plug 240 may obstruct further fluid flow through the medical plug 240. As the flow rate of fluid through the medical plug 240 decreases, a greater proportion of the fluid may instead pass through the second pathway (i.e., through the bypass channel 264) to enter into the reservoir 207 of the syringe 202.

Relative flow rates between the two pathways may depend on a variety of factors, such as the composition of the medical plug 240 and the cross-sectional surface areas presented by the primary channel 262 and the bypass channel 264. For example, in some embodiments, the cross-sectional surface area of the primary channel 262 (where the cross-section is perpendicular to the longitudinal axis of the medical plug delivery device 200) is greater than the cross-sectional surface area of the bypass channel 264. Thus, a relatively large fluidic force may be applied to the medical plug 240 (during both retraction and advancement of the plunger 206) due to its positioning within a channel (i.e., the primary channel 262) having a relatively large cross-sectional surface area in comparison with the cross-sectional surface area of the bypass channel 264.

If desired, any air bubbles that were introduced into the medical plug delivery device 200 as the plunger 206 was retracted may be removed in the traditional manner (i.e., by orienting the medical plug delivery device 200 such that the distal end of the medical plug delivery device 200 is pointed upward, tapping the medical plug delivery device 200, and ejecting air bubbles by advancing the plunger 206 toward the distal end of the medical plug delivery device 200).

In some circumstances, once both the medical plug 240 has been wetted and a sufficient quantity of fluid has entered into the reservoir 207 of the syringe 202, the practitioner may couple the distal channel 248 to an elongate tube, such as an introducer sheath or catheter. The elongate tube may be in fluid communication with a void into which the medical plug 240 is to be inserted. For example, the distal adaptor 214 may be coupled to a proximal end of an introducer sheath used in a biopsy procedure as described above. The practitioner may rotate the selector 210 one position to a first ejection position. The rotation to the first ejection position may be confirmed by a tactile and an audible feedback. The practitioner may then advance the plunger 206 toward the distal end of the syringe 202, thereby displacing fluid in a distal direction.

As the fluid is displaced in a distal direction, the fluid may be expelled from the syringe 202, travel through the proximal channel 247 of the selector 210 to the chamber 231, and exert a distal force on the medical plug 240 disposed therein, thereby causing distal displacement and ejection of the medical plug 240 from the magazine 230. The medical plug 240 may then continue onward, travelling through the guide channel 249, the distal channel 248, and an elongate tube that is coupled to the distal channel 248 to be placed within a void of the patient. The inserted medical plug 240 may serve any suitable purpose, such as obstructing fluid flow, inducing blood coagulation, and/or providing a scaffold to promote tissue growth.

In some embodiments or circumstances, instead of retracting the plunger 206 to draw fluid into the reservoir 207 of the syringe 202 as described above, the syringe 202 may be pre-filled with liquid. The distal end of the pre-filled syringe 202 may then be attached to a proximal end of the selector 210. Once the syringe 202 is attached to the proximal channel 247, the plunger 206 may be advanced. Advancement of the plunger 206 in this manner may both wet the particular medical plug 240 and discharge the medical plug 240 from the medical plug delivery device 200 into an elongate tube for delivery to a void as described above. In other words, the medical plugs 240 may be hydrated as they are ejected from the magazine 230 instead of being wetted by retraction of the plunger 206.

Once the first medical plug 240 has been deployed from the first chamber 231, the medical plug delivery device 200 may be transitioned to a different configuration in which the second chamber 232 is in fluid communication with the proximal channel 247 of the selector 210. To transition the medical plug delivery device 200 to this configuration, the practitioner may apply a rotational force to the selector 210, thereby causing the selector 210 to be rotationally displaced relative to magazine 230. Such rotational displacement of the selector 210 with respect to the magazine 230 may cause a transition from a first ejection configuration in which the first chamber 231 is in fluid communication with the distal channel 248 to a second ejection configuration in which the second chamber 232 is in fluid communication with the distal channel 248 of the selector 210.

Once the selector 210 and the magazine 230 are positioned such that the second chamber 232 of the magazine 230 is aligned with the proximal channel 247, the practitioner may wet and deploy a second medical plug 240 from the second chamber 232 in a manner analogous to that described above in connection with the first medical plug 240 that was disposed within the first chamber 231. Once the second medical plug 240 has been deployed, the selector 210 may be further rotated relative to the magazine 230 to enable wetting and deployment of a third medical plug 240 from the third chamber 233. Medical plugs within the fourth chamber 234 and the fifth chamber 235 may be wetted and deployed by analogous methods. A skilled artisan will recognize that magazines 230 that include any number of medical plugs 240 are contemplated and within the scope of this disclosure.

In the depicted embodiment, the medical plug delivery device 200 is configured to rotate in a counterclockwise direction (as viewed from the proximal end of the medical plug delivery device 200). The medical plug delivery device 200 is configured to rotate around the elongate member 224 in only a single direction. Rotation in a clockwise direction may be prevented by the interface of the square face of the recesses 270, 271, 272, 273, 274, 275 with the square face of the detent 219. Further, in some embodiments, the medical plug delivery device 200 may include a stop (e.g., an obstruction) (not shown) that prevents more than one rotation of the selector 210 about the elongate member 224. Embodiments that both permit only unidirectional rotation of the selector 210 and include a stop such as the stop described above may prevent a practitioner from unintentionally returning to a chamber 231, 232, 233, 234, 235 from which a composition or medical article has already been deployed.

The medical plug delivery device 200 may be manufactured via any suitable method. For example, in some embodiments, a method of manufacturing the medical plug delivery device 200 comprises insertion of a plurality of cartridges 260 into the chambers 231, 232, 233, 234, 235 of the magazine 230. Each of the cartridges 260 may be attached to one of the chambers 231, 232, 233, 234, 235 via an adhesive. In some embodiments the shouldered cylinder 220 is disposed in the central lumen 236 of the magazine 230. The guide 250 may be attached to the magazine 230. The elongate member 224 may then be inserted through the selector 210, through the central lumen 236 of the magazine 230, and into the shouldered cylinder 220 such that the elongate member 224 engages threads in the shouldered cylinder 220 and the selector 210 is rotatably coupled to the magazine 230.

Figure 15:
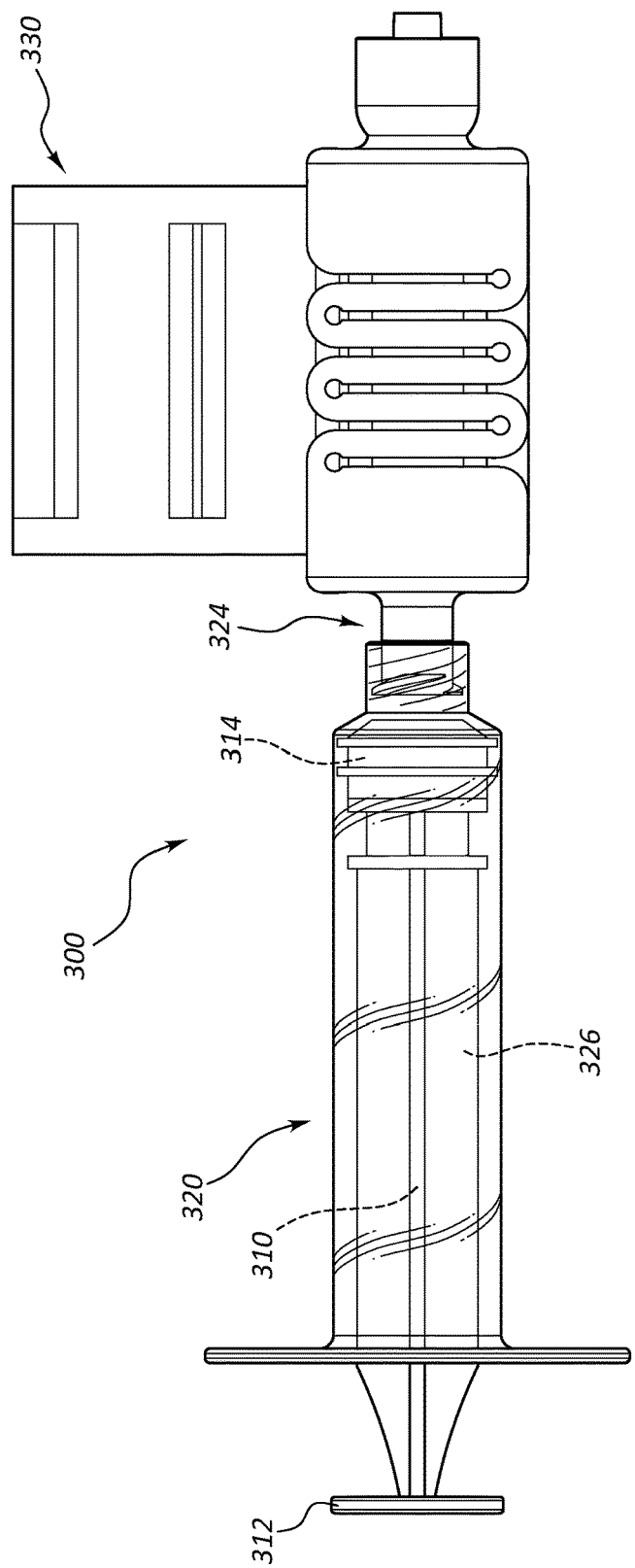
FIG. 15 is a side view of another embodiment of a medical device for delivering a plug.

FIG. 15 provides an annotated photograph of a medical device 300 for delivering a plurality of plugs to one or more interior regions of a patient. As depicted in FIG. 15, the medical device 300 may include a plunger 310, a syringe body 320, and a plug holder 330.

The plunger 310 may include a handle 312 adjacent the proximal end of the plunger 310, and a seal 314 adjacent the distal end of the plunger 310. The plunger 310 may be configured to be at least partially disposed within the syringe body 320 such that advancement and retraction of the plunger 310 causes displacement of fluid within a reservoir 326 of the syringe body 320. The syringe body 320 may be configured to couple to a proximal end of the plug holder 330. For example, in the depicted embodiment, the syringe body 320 includes a male Luer connection at its distal end 324. The plunger 310 and the syringe body 320 may be components of standard, commercially available syringes. The syringe body 320 may be capable of holding enough fluid to facilitate deployment of multiple plugs into a patient. For example, in some embodiments, the syringe body 320 is capable of holding at least 5 mL or at least 10 mL of fluid.

Figure 16:
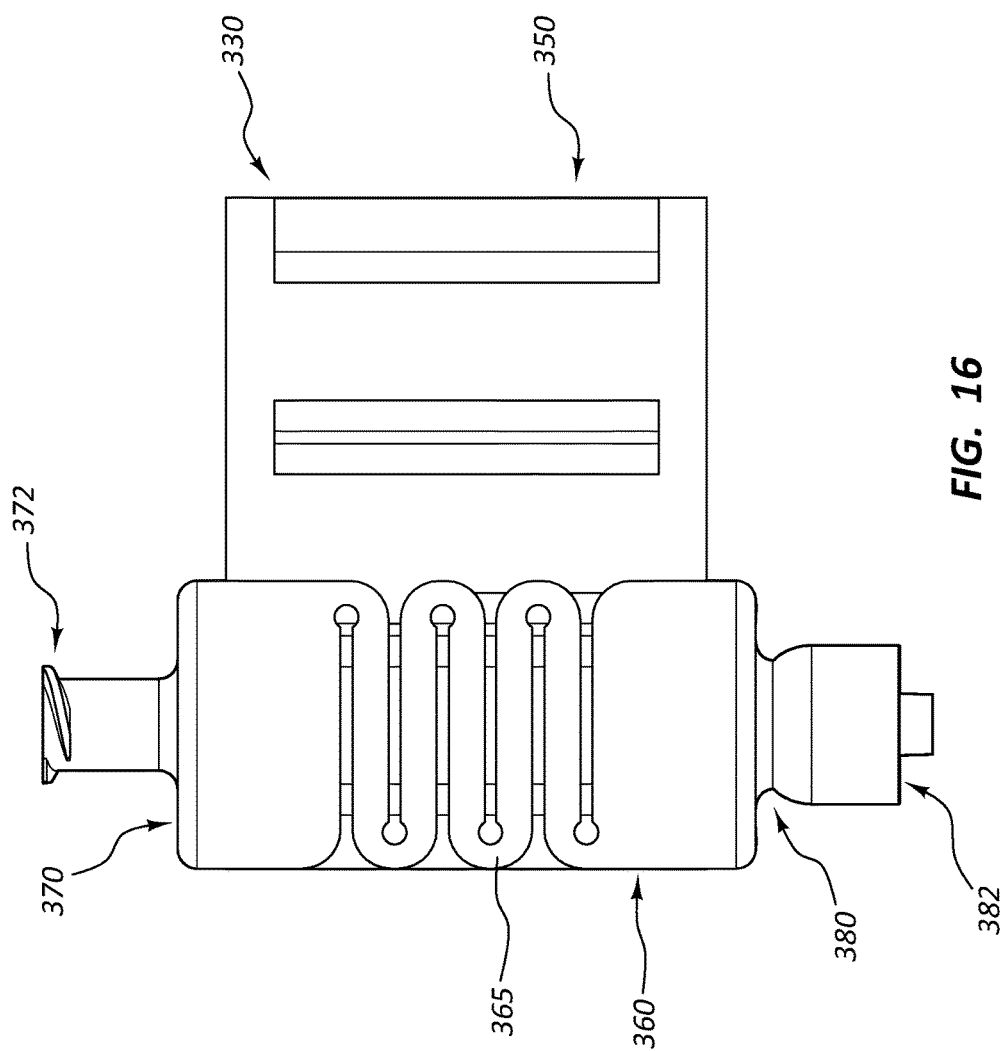
FIG. 16 is a front view of a plug holder for the medical device of FIG. 15.
Figure 17:
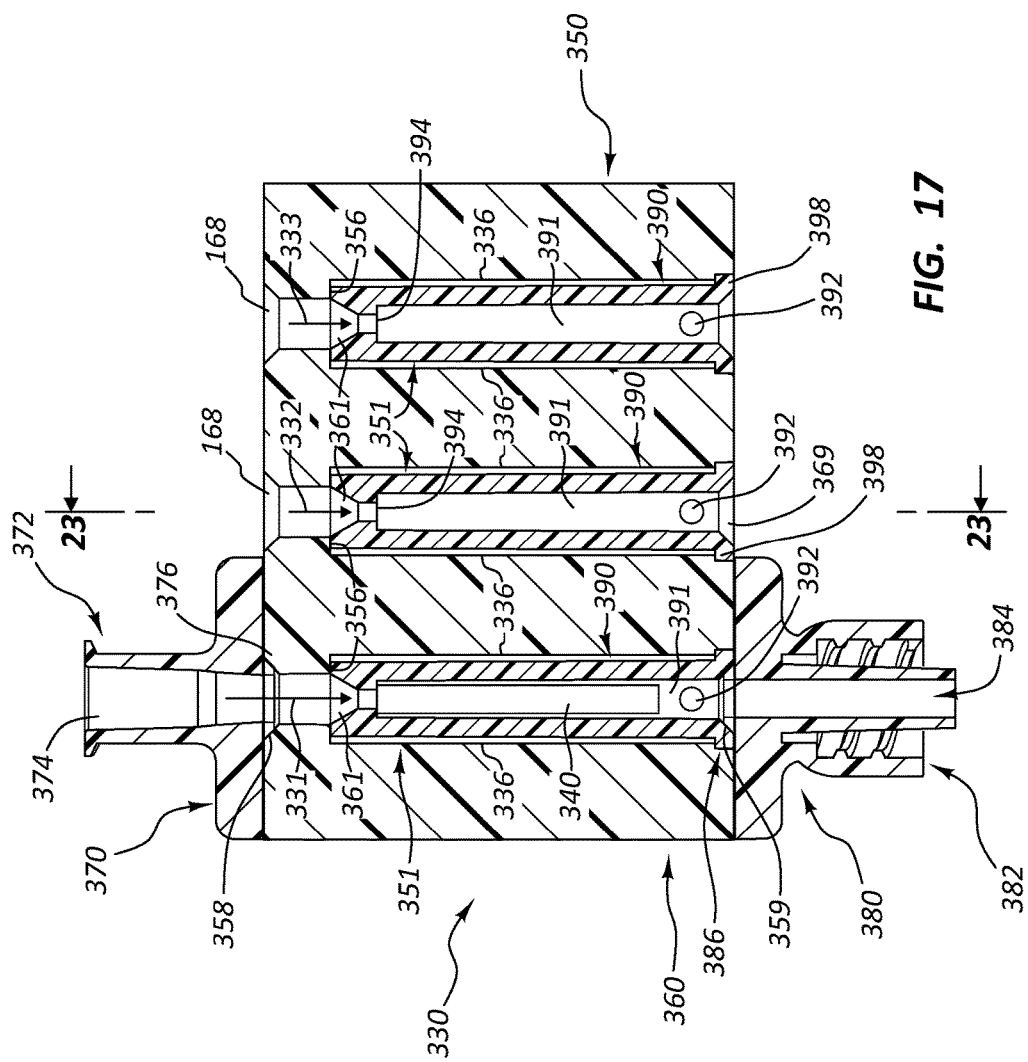
FIG. 17 is a cross-sectional front view of the plug holder of FIG. 16 taken through plane 17-17 of FIG. 18.
Figure 18:
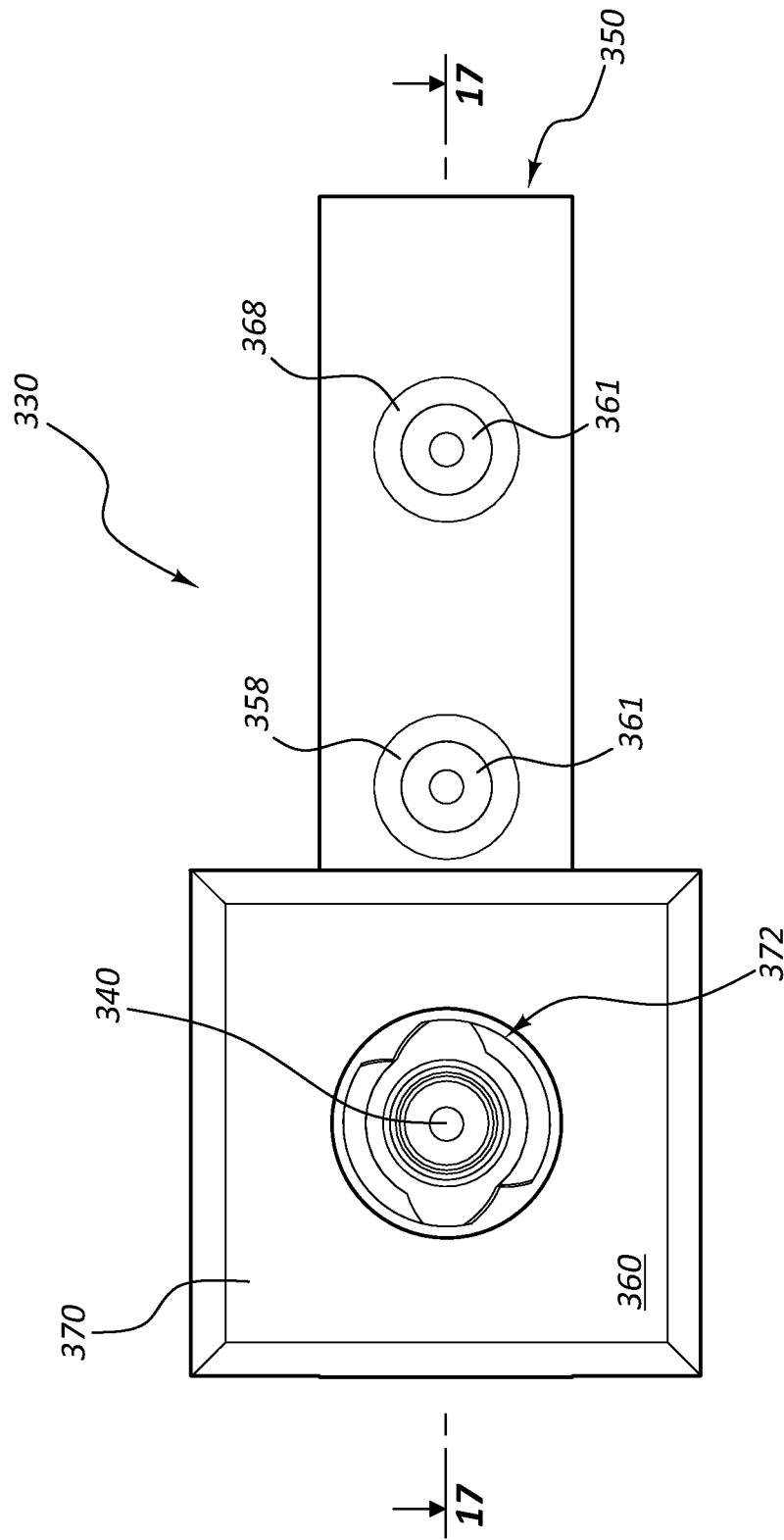
FIG. 18 is a top view of the plug holder of FIGS. 16 and 17.
Figure 19:
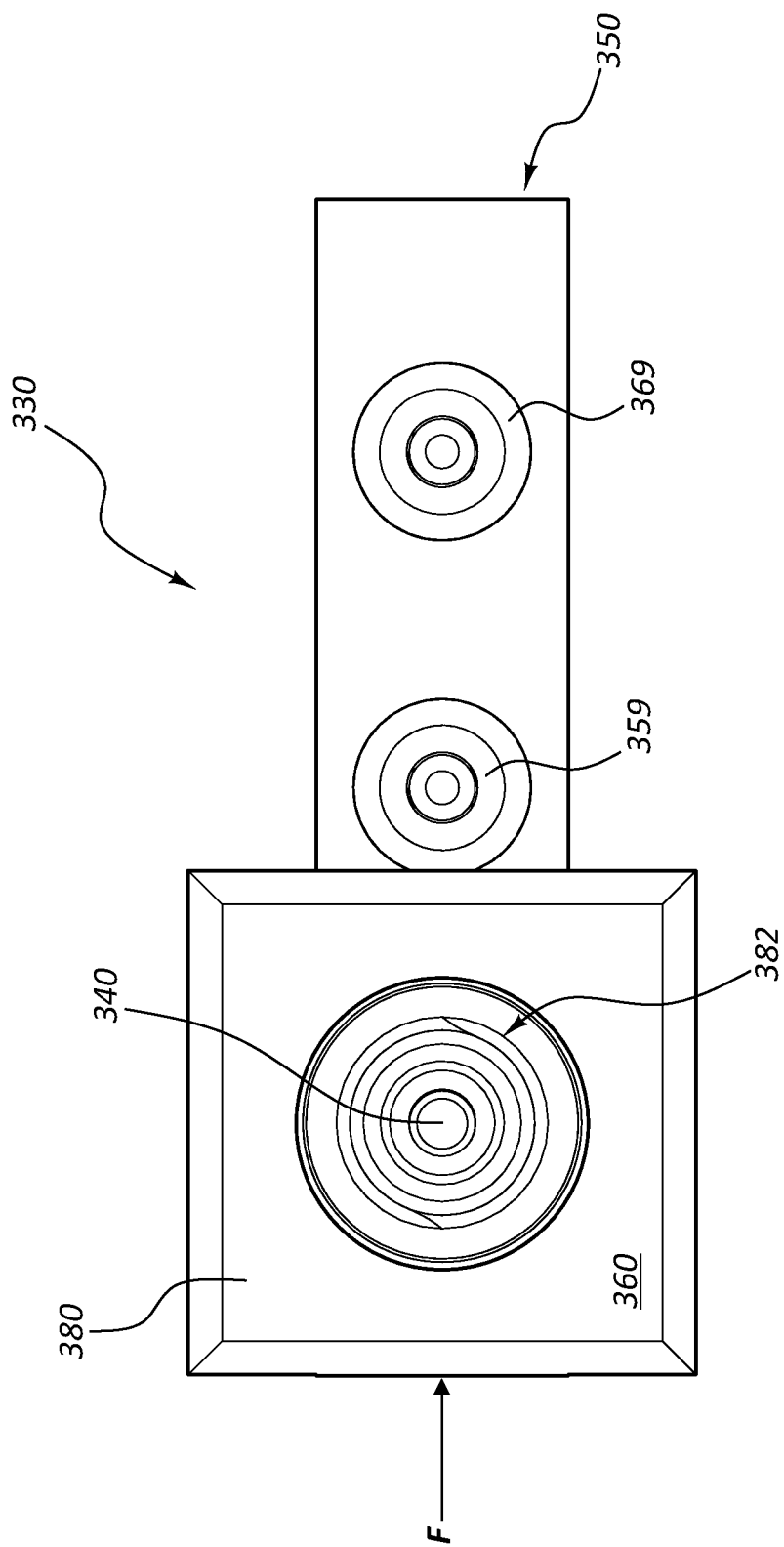
FIG. 19 is a bottom view of the plug holder of FIGS. 16-18.
Figure 20:
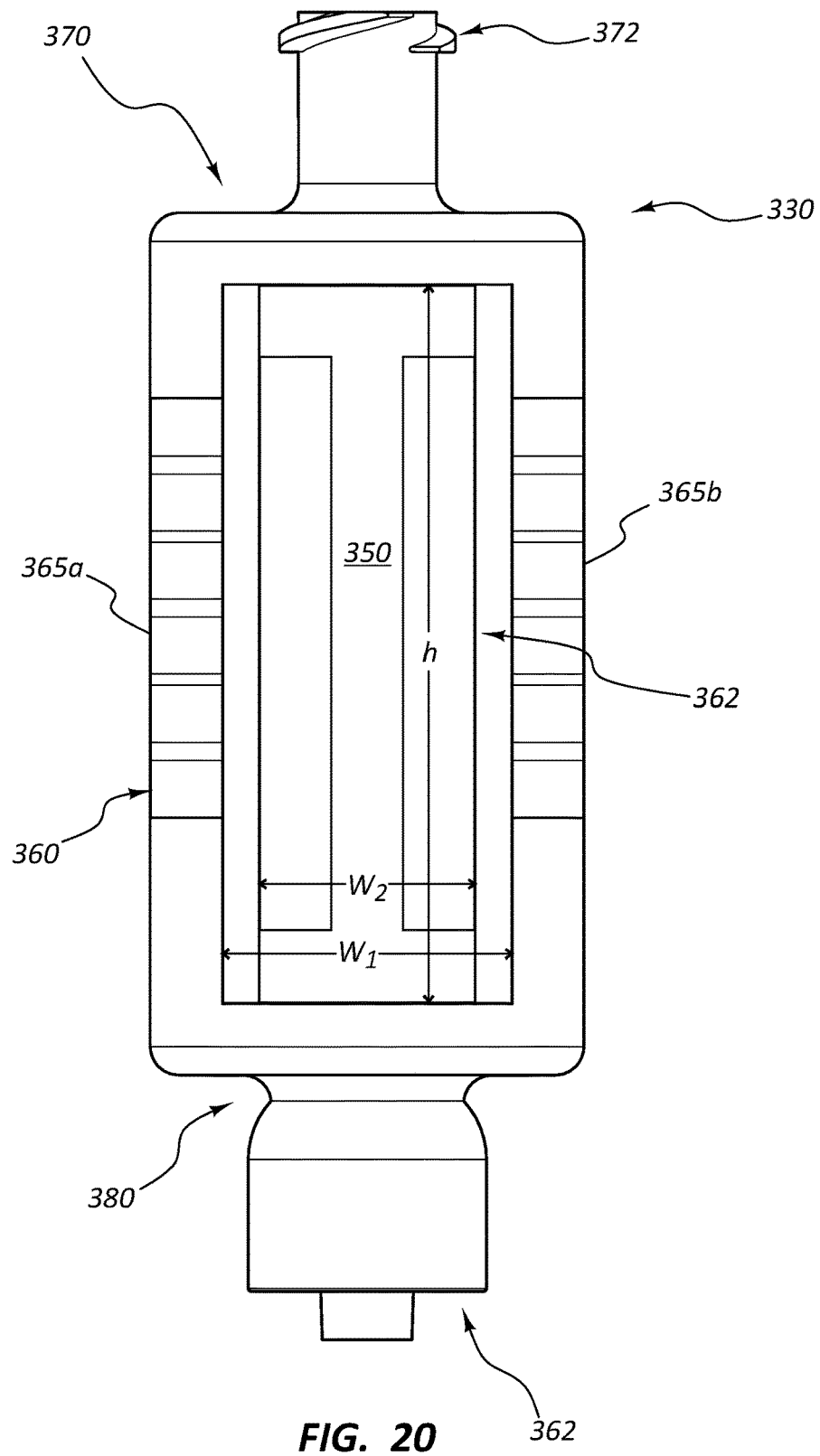
FIG. 20 is a side view of the plug holder of FIGS. 16-19.
Figure 21:
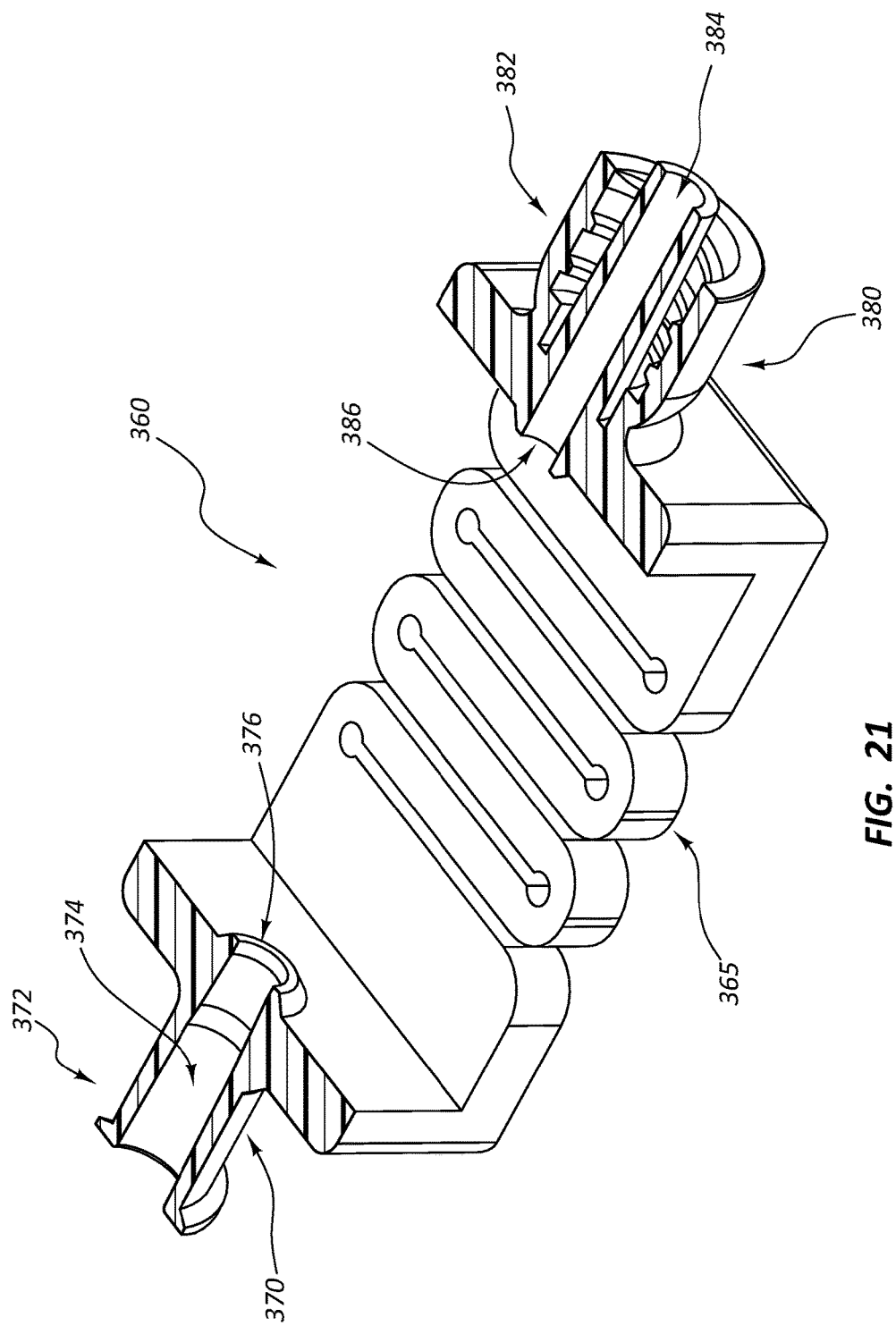
FIG. 21 is a cross-sectional perspective view of a resilient adaptor of the plug holder of FIGS. 16-20, taken through a plane in the position indicated by plane 17-17 of FIG. 18.
Figure 22:
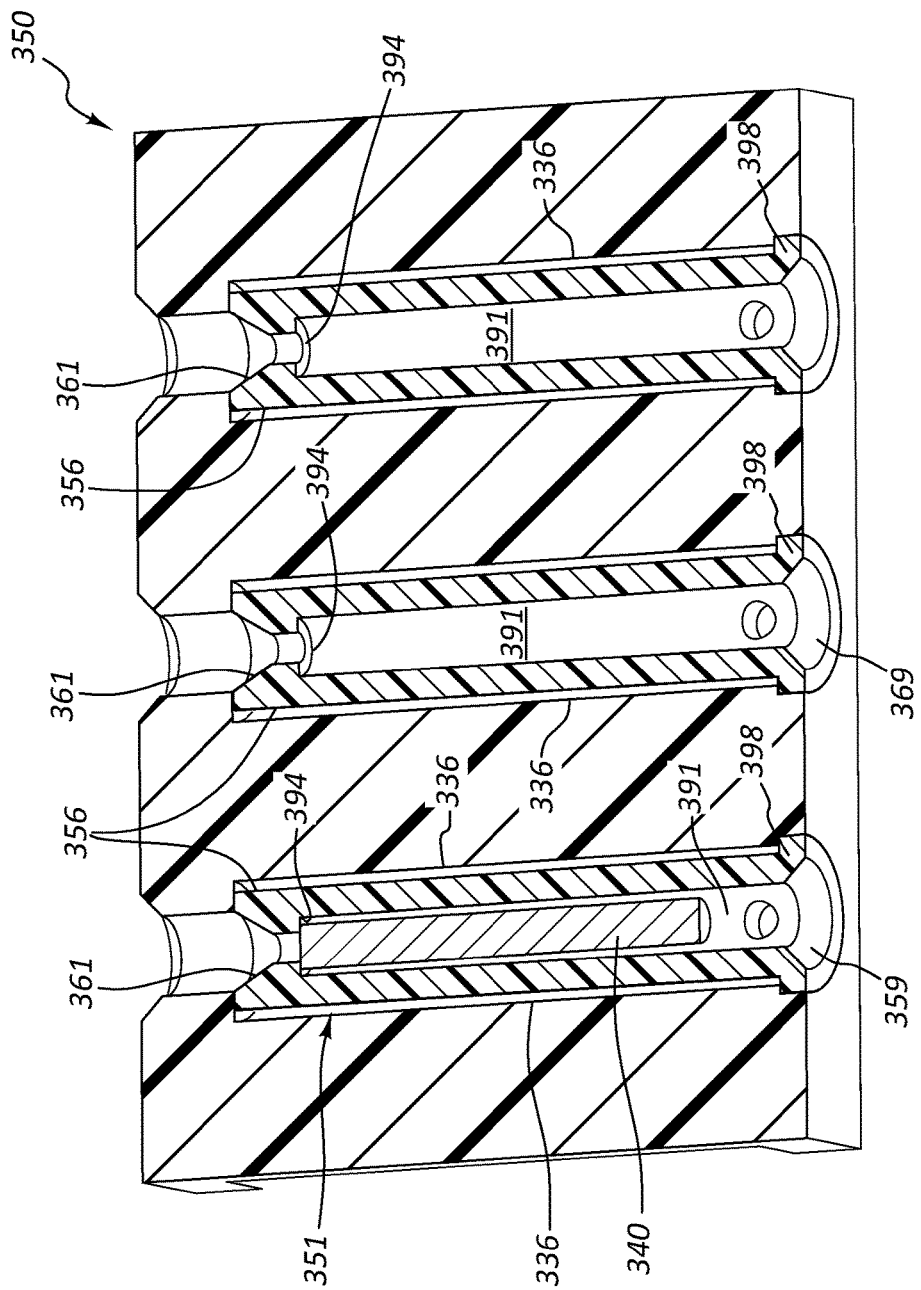
FIG. 22 is a cross-sectional view of a plug magazine of the plug holder of FIGS. 16-21, taken through a plane in the position indicated by plane 17-17 of FIG. 18.
Figure 23:
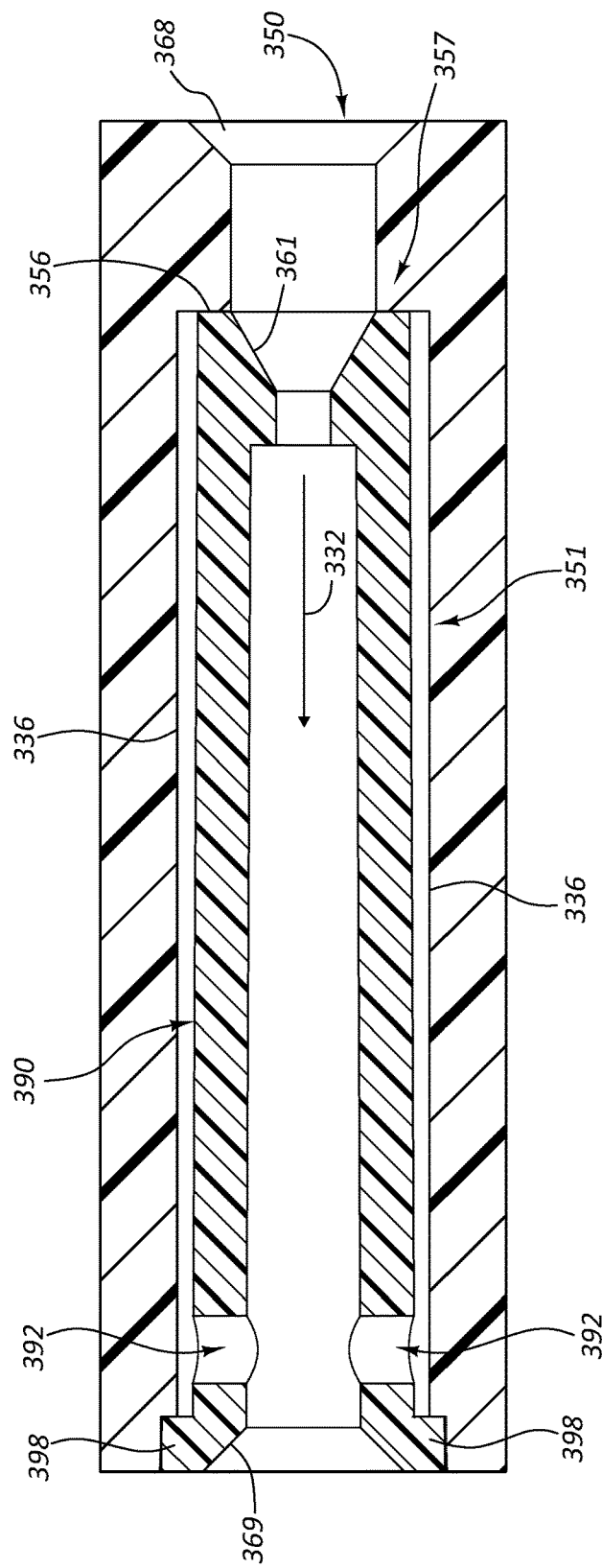
FIG. 23 is a cross-sectional view of a plug magazine of the plug holder of FIGS. 16-22 taken through plane 23-23 of FIG. 17.

The plug holder 330 may be configured to couple to the distal end 324 of the syringe body 320. The plug holder 330 is shown in further detail in FIGS. 16-23. More particularly, FIG. 16 provides a front view of the plug holder 330. FIG. 17 provides a cross-sectional front view of the plug holder 330, taken through plane 17-17 of FIG. 18. FIGS. 18 and 19 provide top (FIG. 18) and bottom (FIG. 19) views of the plug holder 330. FIG. 20 provides a side view of the plug holder 330. FIG. 21 is a cross-sectional perspective view of a resilient adaptor 360 of the plug holder 330 taken through a plane in the position indicated by plane 17-17 of FIG. 18. FIG. 22 is a cross-sectional perspective view of a plug magazine 350, a plug 340, and plug cartridges 390 of the plug holder 330 taken through a plane in the position indicated by plane 17-17 of FIG. 18. FIG. 23 is a cross-sectional view of the plug magazine 350 through line 23-23 of FIG. 17.

As shown in FIGS. 16-23, the plug holder 330 may include the plug magazine 350 and a resilient adaptor 360. In the depicted embodiment, the plug magazine 350 is a solid rectangular prism with a plurality of parallels cavities 351 that extend from one side of the plug magazine 350 to an opposite side of the plug magazine 350. The plug magazine 350 may be configured to hold a plurality of plugs 340. For example, a plug 340 may be disposed in each of the cavities 351 of the plug magazine 350. In some embodiments, the plug holder 330 (or a portion thereof) is substantially transparent, thereby allowing the practitioner to view the wetting and ejection of the plug 340 as described below. In other embodiments, the plug holder 330 is opaque. In the illustrated embodiment, one plug 340 is shown in one cavity 351 of the plug magazine 350. Embodiments wherein a plug 340 is in each cavity 351 are also within the scope of this disclosure.

The plugs 340 may be of any suitable composition, shape, and/or size. For example, in some embodiments, the plugs 340 include, comprise, or consist essentially of a bioabsorbable material. In some embodiments, the bioabsorbable material (or a portion thereof) is derived from animal tissue, such as pig skin or cow skin. In some embodiments, the bioabsorbable material is a collagen-containing material, such as a gelatin foam from an animal source. In other or further embodiments, the bioabsorbable material (or a portion thereof) is a synthetic polymer, such as polylactic acid, polyglycolide, or poly(lactic-co-glycolic acid). In some embodiments, the plugs 340 include or consist essentially of a non-bioabsorbable material, such as polyvinyl alcohol or polyvinyl acetate. In some embodiments, the plugs 340 include a dye. The dye may facilitate visualization of the plugs 340 when the plugs 340 are disposed within the plug holder 330. In some embodiments, the plug 340 may change colors when contacted with fluid (e.g., water or saline), thereby allowing a practitioner to visually determine when the plug 340 has been wetted.

The plug 340 may be generally elongate in shape. For example, in some embodiments, the plug 340 is an elongate piece of material that has been rolled into a substantially cylindrical shape of between 1 mm and 5 mm (e.g., approximately 2 mm) in diameter. The plug 340 may have a length that is at least two-fold, at least five-fold, and/or at least 10-fold longer than the diameter of the plug 340. In some embodiments, the plug is between 10 mm and 30 mm (e.g., approximately 20 mm) in length.

The plugs 340 may be disposed within the plug magazine 350 in any suitable manner. For example, in the depicted embodiment, the plug magazine 350 is designed to accommodate a plurality of plug cartridges 390, with each plug cartridge 390 housing a single plug 340. (Although only one plug 340 is shown in the depicted plug magazine 350, the depicted magazine 350 may hold three plugs 340, with one plug 340 in each plug cartridge 390.) While the plug magazine 350 and the plug cartridges 390 are depicted as separate components, one of ordinary skill in the art will recognize that, in some embodiments, the plug magazine 350 and plug cartridges 390 may be combined into one integrally formed component. For example, in some embodiments, the plug holder 330 is an integrally formed component that does not include any apertures or gaps analogous to apertures 392 and an annular gap 336 shown in the depicted embodiment.

In some embodiments, each of the cavities 351 of the plug magazine 350 includes a distal portion that is sized to accommodate a plug cartridge 390. In other words, a plug cartridge 390 may be disposed within a distal portion of each cavity 351. The plug cartridges 390 may be generally elongate in shape with a hollow interior such that a flow path 331, 332, or 333 extends longitudinally through each plug cartridge 390.

As shown in FIG. 17, the plug cartridge 390 may include a distal protrusion 398 (e.g., an annular protrusion) that contacts an inner diameter of the cavity 351. In some embodiments, the distal protrusion 398 contacts the inner diameter of the cavity 351 to form an interference fit. In other embodiments, the distal protrusion 398 is attached to the plug magazine 350 via an adhesive. The size of the protrusion 398 extending radially outward relative to the remaining portion of the plug cartridge 390, may be configured such that an annular gap 336 may be formed between an inner diameter of the plug magazine 350 and an outer diameter of the plug cartridge 390. In some embodiments, the annular gap 336 is part of an alternative flow path in which fluid travels from the proximal end of the plug magazine 350, around the exterior surface of the plug cartridge 390, and through one or more distal apertures 392 of the plug cartridge 390 to exit from the plug holder 330 without passing through the plug 340. However, in other embodiments, no alternative flow path is available. Fluid flow in either direction (proximal to distal or distal to proximal) through this alternative flow path is within the scope of this disclosure. Further, one or more openings may be positioned between the proximal end of the plug cartridge 390 and a ledge 356 of the plug magazine (such as due to a longitudinal offset between the proximal end of the plug cartridge 390 and the ledge 356) to allow fluid communication along the alternative flow path.

In some embodiments, the plug cartridge 390 includes a frustoconical surface 361 adjacent its proximal end. The frustoconical surface 361 may direct (e.g., funnel) fluid flow into a first flow path 331 as the plug 340 is deployed as described below.

The plug cartridge 390 may also include a shoulder 394 that is configured to restrict proximal displacement of the plug 340 during operation of the medical device 300. In the depicted embodiment, the shoulder 394 is an annular protrusion that extends inward from the plug cartridge 390. The shoulder 394 may define a proximal portion of a plug cartridge lumen 391 that is relatively narrow in comparison to a distal portion of the plug cartridge lumen 391. In other words, a proximal portion of the plug cartridge lumen 391 that is defined by the shoulder 394 may have a smaller diameter than a distal portion of the plug cartridge lumen 391.

The plug magazine 350 may include a ledge 356 adjacent a proximal end of the plug magazine 350. The ledge 356 may be designed to contact the plug cartridge 390, thereby preventing movement of the plug cartridge 390 past the ledge 356. As described above, in some embodiments there may be offsets, openings, or passageways that create fluid communication between the portion of the first flow path 331 proximal of the ledge 356 and the annular space or gap 336 between the plug cartridge 390 and the plug magazine 350.

The resilient adaptor 360 may be configured to receive the plug magazine 350 and slide along the plug magazine 350 to sequentially deploy various plugs 340. The resilient adaptor 360 may include a proximal portion 370, a distal portion 380, and one or more springs 365 disposed between the proximal portion 370 and the distal portion 380.

The proximal portion 370 of the resilient adaptor 360 may include a proximal adaptor 372 that is configured to couple to the distal end 324 of the syringe body 320. For example, the proximal portion 370 may include a female Luer connection that mates with a male Luer connection at the distal end 324 of the syringe body 320 to form a fluid-tight connection. The proximal portion 370 may also include a distally extending frustoconical protrusion 376 and/or a lumen 374 that extends through the proximal portion 370.

The distal portion 380 may include a distal adaptor 382. In the depicted embodiment, the distal adaptor 382 includes a male Luer lock connection. The distal adaptor 382 may be configured to couple to a proximal end of an elongate tube, such as an introducer sheath or catheter, for delivery of one or more plugs 340 into a patient. The distal portion 380 may also include a proximally extending frustoconical protrusion 386 and/or a lumen 384 that extends through the distal portion 380.

The one or more springs 365 of the resilient adaptor 360 may be coupled to and extend between the proximal portion 370 and the distal portion 380. For example, in the depicted embodiment, a first spring 365a and a second spring 365b are disposed on opposite sides of a channel 362 that extends between the springs 365a, 365b (see FIG. 6). When the one or more springs 365 are in a resting state, the height of the channel 362 may approximate (or be slightly shorter than) the height (h) of the plug magazine 350. The width of the channel ($w_1$) may be at least as long as the width ($w_2$) of the plug magazine 350. Note the reference numeral 365 is used to refer to the springs 365 generally, while the numerals 365a and 365b refer specifically to springs on either side of the resilient adaptor 360 as shown in FIG. 6. Further, the difference in height between the height of the channel 362 and the height of the plug magazine 350 may be configured such that the spring 365 exerts a compressive force on the plug magazine 350. This compressive force may provide a force associated with audible and/or tactile feedback when the plug magazine 350 is displaced with respect to the resilient adaptor 360 (as further detailed below) and/or may provide a force associated with creating a fluid-tight seal between portions of the plug magazine 350 and resilient adaptor 360 (as also detailed below).

The spring 365 may be any suitable spring. For example, the spring 365 may be made from any suitable material, such as an elastic polymer or a wire. In the depicted embodiment, the spring 365 is a substantially planar spring that is formed from an elastomeric material that has been shaped or cut into a serpentine pattern. The material and shape of the spring 365 may allow it to stretch when tension is applied to both the proximal portion and the distal portion of the spring 365. Further, the resiliency of the spring 365 may bias the spring 365 to return to a more compact configuration. Springs 365 of different shapes are also within the scope of this disclosure. Stated another way, the resilient adaptor 360 may comprise a compliant mechanism comprising the spring 365 and other elements.

The plug magazine 350 may be disposed within the resilient adaptor 360 as shown in the illustrated embodiment. In the configuration depicted in the figures, the lumen 374 of the proximal portion 370 and the lumen 384 of the distal portion 380 of the resilient adaptor 360 are aligned with a first flow path 331 that extends through the plug magazine 350.

To deploy a first plug 340 from the plug magazine 350, a practitioner may obtain a syringe that includes a plunger 310 and a syringe body 320 that is filled with sufficient fluid in its reservoir 326 to deploy a desired number of plugs 340. The practitioner may then attach the plug holder 330 to the distal end 324 of the syringe body 320 and couple the distal end of the plug holder 330 to an elongate tube, such as an introducer sheath or catheter. The elongate tube may be in fluid communication with a void into which the plug 340 is to be inserted. For example, the distal end 324 of the syringe body 320 may be coupled to a proximal end of an introducer sheath used in a biopsy procedure as described above. The practitioner may then advance the plunger 310 toward a distal end 324 of the syringe body 320, thereby distally displacing fluid in the reservoir 326.

In some embodiments, as the fluid is displaced in a distal direction, the fluid may encounter the frustoconical surface 361 of the plug cartridge 390. The frustoconical surface 361 may direct (e.g., funnel) fluid along the flow path 331. As the fluid follows the first flow path 331, the fluid may exert a distal force on the plug 340 disposed within the plug magazine 350, thereby causing distal displacement and ejection of the plug 340 from the plug holder 330 into the elongate tube that is in fluid communication with the void. The fluid may also wet the plug 340, which may increase the lubricity of the plug 340. In other words, the plug 340 may be hydrated as it is ejected from the plug holder 330. In some circumstances, wetting of the plug 340 may cause the plug 340 to swell. As the plunger is further advanced, the displaced fluid may push the plug 340 through the elongate tube and into the desired void. The inserted plug 340 may serve any suitable purpose, such as obstructing fluid flow, inducing blood coagulation, and/or providing a scaffold to promote tissue growth.

Once the first plug 340 has been deployed, the plug holder 330 may transition to a different configuration in which the lumen 374 of the proximal portion 370 and the lumen 384 of the distal portion 380 are aligned with a second flow path 332. To transition the plug holder 330 to this configuration, the practitioner may apply a lateral force (F, see FIG. 5) on the resilient adaptor 360 while restraining movement of the plug magazine 350. As the lateral force is applied to the resilient adaptor 360, the frustoconical protrusion 376 may slide along a first sloped surface 358, and the frustoconical protrusion 386 may slide along a second sloped surface 359. Due to the direction of these sloped surfaces 358, 359, the distance between the proximal portion 370 and the distal portion 380 of the resilient adaptor 360 increases as the resilient adaptor 360 is initially displaced relative to the plug magazine 350, thereby causing extension of the spring 365.

As the resilient adaptor 360 approaches the second flow path 332, the frustoconical protrusions 376, 386 may slide along a third sloped surface 368 and a fourth sloped surface 369 such that the resilient adaptor 360 is guided to a position in which the proximal lumen 374 and the distal lumen 384 are aligned with the second flow path 332. The spring 365 may provide a force that facilitates seating of the frustoconical protrusions 376, 386 in the region occupied by the sloped surfaces 368, 369. For example, in some embodiments, the spring 365 may cause the plug holder 330 to snap into place, thereby providing the practitioner with tactile and/or audible feedback that the resilient adaptor 360 is properly aligned for deployment of another plug 340.

Once the resilient adaptor 360 is positioned such that the proximal lumen 374 and the distal lumen 384 are aligned with the second flow path 332, the practitioner may deploy the second plug 340 in a manner analogous to that described above in connection with the first plug 340. The resilient adaptor 360 may be further slid relative to the plug magazine 350 to enable deployment of a third plug 340. A skilled artisan will recognize that plug magazines 350 that include any number of plugs 340 are contemplated and within the scope of this disclosure.

Additionally, the spring 365 may provide a compressive force that tends to force the frustoconical protrusions 376, 386 of the resilient adaptor 360 into contact with the mating sloped surfaces (358, 359 when the magazine 350 is in the position shown in the figures) such that the mating surfaces, and the force applied thereon, form a fluid-tight seal when the proximal lumen 374 and the distal lumen 384 are aligned with one of the flow paths 331, 332, 333. This may facilitate use of the assembly without additional seals such as o-rings.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure.

This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A device for delivering medical plugs to a patient, the device comprising:
   a magazine defining a plurality of chambers disposed around a longitudinal axis of the magazine, the plurality of chambers further configured to house a medical plug in each chamber;
   a proximal port coupled to a proximal end of the magazine, the proximal port configured to be coupled to a fluid delivery device; and
   a distal port coupled to a distal end of the magazine, the distal port configured to be coupled to a lumen in communication with a patient,
   the magazine configured such that fluid flow from the proximal port to the distal port is configured to eject a medical plug from the magazine;
   a selector that is coupled to the magazine such that the selector and the magazine are configured to rotate about the longitudinal axis of the device relative to each other, the selector comprising a channel that is disposed proximal of the magazine;
   wherein the device is configured such that rotation of the selector relative to the magazine causes the delivery device to transition from a first configuration in which a distal end of the channel of the selector is not axially aligned with a proximal end of a first chamber of the plurality of chambers to a second configuration in which the distal end of the channel is axially aligned with the proximal end of the first chamber;
   a detent that extends distally from the selector, wherein the detent is configured to rotate with the selector upon rotation of the selector relative to the magazine; and
   a plurality of recesses in the magazine, wherein the recesses are disposed adjacent a proximal end of the magazine, and wherein the recesses are configured to receive the detent;
   wherein the device is configured such that a distal tip of the detent extends further from the selector when the detent is disposed within a recess of the plurality of recesses than when the detent is positioned between adjacent recesses of the plurality of recesses;
   wherein the number of recesses in the magazine is more than the number of chambers in the magazine.

2. The device of claim 1, wherein the selector is configured to rotate relative to the magazine in only a single direction.

3. The device of claim 1, wherein each recess of the plurality of recesses comprises a sloped surface and a shoulder such that rotation of the selector relative to the magazine is permitted in only a single direction.

4. The device of claim 1, wherein interaction between the magazine and one or both of the detent and the selector provides audible and/or tactile feedback to indicate that a proximal end of a chamber of the plurality of chambers is axially aligned with the distal end of the channel of the selector.

5. The device of claim 1, wherein the distal end of the channel is aligned with a cavity of the magazine that does not extend through the magazine when the device is in the first configuration.

6. The device of claim 5, wherein a gap is disposed between a portion of the magazine and a portion of the selector such that fluid passing distally through the channel when the device is in the first configuration causes fluid to enter into the cavity of the magazine, flow into the gap, and enter into each chamber of the plurality of chambers.

7. The device of claim 1, further comprising a guide disposed distal of the magazine, wherein each chamber of the plurality of chambers is in fluid communication with the guide such that fluid passing distally through any chamber of the magazine exits the device through a single opening at the distal end of the guide.

8. The device of claim 7, wherein the distal end of the channel of the selector is not axially aligned with the single opening at the distal end of the guide.

9. The device of claim 1, further comprising:
   a syringe coupled to the proximal adaptor of the selector, wherein the distal adaptor that is coupled to a guide, and wherein the distal adaptor is configured for coupling to an elongate tube for delivery of a medical plug to a patient.

10. The device of claim 1, wherein the device is configured to transition from the second configuration to a third configuration in which the distal end of the channel of the selector is axially aligned with a proximal end of a second chamber of the plurality of chambers.

11. The device of claim 1, wherein the selector further comprises a second channel that is disposed distal of the magazine and a connecting region disposed between the channel that is disposed proximal of the magazine and the channel that is disposed distal of the magazine, wherein the selector provides a compressive force for facilitating a fluid-tight seal between the selector and a chamber of the plurality of chambers.

12. A medical plug delivery device comprising:
   a magazine comprising a first chamber and a second chamber; and
   a selector coupled to the magazine, the selector comprising a fluid channel, wherein the selector is configured such that manipulation of the selector causes the channel to be displaced from a configuration in which a distal end of the channel is axially aligned with a proximal end of the first chamber to a configuration in which the distal end of the channel is axially aligned with a proximal end of the second chamber;
   wherein the magazine and the selector are coupled to each other to form an enclosure that defines a gap between a portion of the magazine and a portion of the selector, wherein the gap is in fluid communication with both of the first chamber and the second chamber when the device is in a first configuration that permits simultaneous delivery of fluid to the first chamber and the second chamber.

13. The medical plug delivery device of claim 12, wherein the selector is rotatably coupled to the magazine to permit rotation of the selector from the first configuration to the configuration in which the distal end of the fluid channel is axially aligned with the proximal end of the first chamber.

14. The medical plug delivery device of claim 12, wherein the gap is not in fluid communication with both of the first chamber and the second chamber when the device is in the configuration in which the distal end of the channel is axially aligned with the proximal end of the first chamber.

* * * * *